United States Patent [19]
Chapple

[11] Patent Number: 5,981,837
[45] Date of Patent: Nov. 9, 1999

[54] METHOD FOR REGULATION OF PLANT LIGNIN COMPOSITION

[75] Inventor: Clint Chapple, West Lafayette, Ind.

[73] Assignee: Purdue Research Foundation, West Lafayette, Ind.

[21] Appl. No.: 09/091,432

[22] PCT Filed: Dec. 19, 1996

[86] PCT No.: PCT/US96/20094

§ 371 Date: Sep. 24, 1998

§ 102(e) Date: Sep. 24, 1998

[87] PCT Pub. No.: WO97/23599

PCT Pub. Date: Jul. 3, 1997

Related U.S. Application Data

[60] Provisional application No. 60/013,388, Mar. 14, 1996, and provisional application No. 60/009,119, Dec. 22, 1995.

[51] Int. Cl.$^6$ .............................. A01H 5/00; C12N 15/82; C12N 5/00; C07H 21/04
[52] U.S. Cl. .......................... 800/278; 435/410; 435/468; 435/469; 536/23.6
[58] Field of Search ................................ 435/468, 469; 435/416; 536/23.6; 800/205

[56] References Cited

U.S. PATENT DOCUMENTS 5,451,514  9/1995  Boudet et al. .......................... 800/286

OTHER PUBLICATIONS

Meyer, K., Cusumano, Joanne C., Somerville, Chris, and Chapple, Clint C.S., "Ferulate–5–hydroxylase from *Arabidopsis thaliana* defines a new family of cytochrome P450–dependent monooxygenases," Proc. Natl. Acad. Sci. USA, vol. 93, pp. 6869–6874, Jul. 1996, Biochemistry.

Chapple, Clint C.S., Vogt, Thomas, Ellis, Brian E., and Somerville, Chris R., "An Arabidopsis Mutant Defective in the General Phenylpropanoid Pathway," The Plant Cell, vol. 4, 1413–1424, Nov. 1992, ©1992 American Society of Plant Physiologists.

Chapple, Clint C.S., "A cDNA Encoding a Novel Cytochrome P450–Dependent Monooxygenase from *Arabidopsis thaliana*," Plant Physiol., vol. 108 pp. 875–876 (1995).

Grand, Claude, "Ferulic acid 5–hydroxylase: a new cytochrome P–450–dependent enzyme from higher plant microsomes involved in lignin synthesis," FEBS Letters, vol. 169, No. 1, pp. 7–11, Published by Elsevier Science Publishers B.V., Apr. 9, 1984, Federation of European Biochemical Societies.

Van Doorsselaere, Jan, Baucher, Marie, Chognot, Emmanuelle, Chabbert, Brigitte, Tollier, Marie–Therese, PetitConil, Michel, Leple, Jean–charles, Pilate, Gilles,Cornu, Daniel, Monties, Bernard, Van Montagu, Marc, Inze, Dirk, Boerjan, Wout and Jouanin, Lise, "A novel lignin in poplar trees with a reduced caffeic acid/5–hydroxyferulic acid O–methyltransferase activity," The Plant Journal, vol. 8, pp. 855–864, 1995.

Dwivedi, Upendra N., Campbell, Wilbur H., Yu, Jun, Datla, Raju S.S., Bugos, Robert C., Chiang, Vincent L., and Podila, Gopi K., "Modification of lignin biosynthesis in transgenic Nicotiana through expression of an antisense O–methyltransferase gene from Populus," Plant Molecular Biology 26:61–71, 1994, Kluwer Academic Publishers, Printed in Belgium.

Goffner, D., Joffroy, I., Grima–Pettenati, J., Halpin, C., Knight, M.E., Schuch, W., and Boudet, A.M., "Purification and characterization of isoforms of cinnamyl alcohol dehydrogenase from Eucalyptus xylem,"Planta (Springer–Verlag) (1992) 188:48–53.

Bell–Lelong, Dolly A., Cusumano, Joanne C., Meyer, Knut and Chapple, Clint, "Cinnamate–4–Hydroxylase Expression in Arabidopsis," Plant Physiol. (1997) 113:729–738.

*Primary Examiner*—Nancy Degen
*Assistant Examiner*—William Sandals
*Attorney, Agent, or Firm*—Woodard, Emhardt, Naughton, Moriarty & McNett

[57] ABSTRACT

A method is disclosed for the regulation of lignin composition in plant tissue. Plants are transformed with a gene encoding an active F5H gene. The expression of the F5H gene results in increased levels of syringyl monomer providing a lignin composition more easily degraded with chemicals and enzymes.

24 Claims, 11 Drawing Sheets

24 hour exposure
1. wild type
2. *fah1-2*

2 hour exposure
3. wild type
4. *fah1-2*
5. line 88
6. line 172
7. line 170
8. line 122
9. line 128
10. line 107
11. line 180
12. line 117
13. line 108

Figure 8B

```
agttattaagttataggaaattattcttttattttttttttttaggaaattattctttgcaacacatttgtcgtttgcaaactt  1890
ttaaaagaaaataaatgattgttataattgattacatttcagttgttatgacagattttttttatctaacctttaatgtttgtttccctgtt  1980
tttaggaaaatcatacaaaatatattgtgatcacagtaaatcacggaatagttatgaccaagatttcaaagtaatacttagaatcct  2070
attaataaacgaaattttaggaagaaataatcaagatttgagcaagtacatgattgttagaagatttgaatctttaattaaat  2160
attttcattcctaaataattaatgctagtggcataataagtcaagtacatgattaatttgttaaaatggtgaaaaatat  2250
atatatgtagattttttcaaaagtatactaattatttcatatttttcaagaaaaatataagaaatggtgtgtacatatgatgaagaa  2340
atttaagtagtaataacaaaaatgtcaaaaaaagggaccacacaatttgattataaaacctacctctctaatcacatcccaaaaTGGAGA  2430
ACTTTGCCTCCTGACAACATTCAGAAAAATAATCGAATCCAAAAAAAACACTCAATATGGAGTCTTCTATATCACAAACACTAAGCAAAC  2520
                                                       M  E  S  S  I  S  Q  T  L  S  K
TATCAGATCCCCAGACGTCTCTTGTCATCGTTGTCTCTCTCTTTCATCAGTTCATCACGGGCGGCGAAGGCCTCCATATCCTC  2610
 L  S  D  P  T  S  L  V  I  V  V  S  L  F  I  F  I  S  F  I  T  R  R  R  P  P  Y  P
CCGGTCCACGAGGTTGGCCATCATAGGCAACATGTTAATGATGGACCAACTCACCCACCGTGGTTTAGCCAATTAGCTAAAAAGTATG  2700
 P  G  P  R  G  W  P  I  I  G  N  M  L  M  M  D  Q  L  T  H  R  G  L  A  N  L  A  K  K  Y
GCGGATTGTGCCATCTCCGACATGGGATTCCTCCATATGTACGCTGTCTCATCACCCGAGGTGGCTCGACAAGTCCTTCAAGTCCAAGACA  2790
 G  G  L  C  H  L  R  M  G  F  L  H  M  Y  A  V  S  S  P  E  V  A  R  Q  V  L  Q  V  Q  D
GCGTCTTCTCGAACCGGCCTGCAACTATAGCTATATCTGACTTACGACGGAGCGGACATGGCTTTCGCTCACTACGGACCGTTTT  2880
 S  V  F  S  N  R  P  A  T  I  A  I  S  Y  L  T  Y  D  R  A  D  M  A  F  A  H  Y  G  P  F
GGAGACAGATGAGAAAGTGTGTCATGAAGTGTTTAGCCGTAAAAGAGCTGAGTCATGGGCTTCAGTTCGTGATGAAGTGGACAAAA  2970
 W  R  Q  M  R  K  V  C  V  M  K  V  F  S  R  K  R  A  E  S  W  A  S  V  R  D  E  V  D  K
TGGTCCGGTCGGTTCTCTTGTAACGTTGGTAAGctacttcacactcttgctatatatgtgcaattaacaaatatgtaaa  3060
 M  V  R  S  V  S  C  N  V  G  K
aagtgaaagtactcatttcttcttttagtatgtacttaacatttaaccaaaacaattgtaggtaagCCTATAAACGTCGGGGAGCA  3150
                                                                   P  I  N  V  G  E  Q
AATTTTGCACTGACCCGCAACATAACTTACCGGGCAGCCGTTTGGGTCAGCCTGCGAGAAGGACAAGACGAGTTCATAAGAATCTTACA  3240
 I  F  A  L  T  R  N  I  T  Y  R  A  A  F  G  S  A  C  E  K  G  Q  D  E  F  I  R  I  L  Q
AGAGTTCTAAGCTTTTTGGAGCCTTCAACGTAGCGGATTCATACCATATTTCGGGTGGATCCGCAAGGGATAAACAAGCGGCT  3330
 E  F  S  K  L  F  G  A  F  N  V  A  D  F  I  P  Y  F  G  W  I  D  P  Q  G  I  N  K  R  L
```

Figure 8C

```
CGTGAAGGCCCGTAATGATCTAGACGGATTTATTGACGATATTATCGATGAACATATGAAGAAGAAGAGAATCAAAACGCTGTGATGA  3420
 V  K  A  R  N  D  L  D  G  F  I  D  D  I  I  D  E  H  M  K  K  E  N  Q  N  A  V  D  D
TGGGGATGTTGTCGATACCGATATGGTTGATGATCTTCTGCTTTTACAGTGAAGAGGCCAAATTAGTCAGTGAGACAGCGGATCTTCA  3510
 G  D  V  V  D  T  D  M  V  D  D  L  L  A  F  Y  S  E  E  A  K  L  V  S  E  T  A  D  L  Q
AAATTCCATCAAACTTACCCGTGACAATATCAAAGCAATCATGGtaattatattcaaaaagcactagtcatagtcatgtttcttaa   3600
 N  S  I  K  L  T  R  D  N  I  K  A  I  I  M
tgcgttacgtaataatacttatccattgaccagttcttctcctaagttttttgttgaattaggaagtaattttctattttactag    3690
agaaagcaacagatttagcatgatctttttttaatatatagaagcattgaatattcagatctacaataattatgaaactaatgaaga  3780
gacaaaaaatggagagagaaaaagagtgtgactagtgtgatatatattcataattctaatttgatttattaggacgttatattaatt  3870
ctaatttgatttttttttattaggACGTTATGTTGGAGGAACGGAAACGGTAGCGTCGGCGATAGAGTGGGCCTTAACGGA          3960
                         D  V  M  F  G  G  T  E  T  V  A  S  A  I  E  W  A  L  T  E
GTTATTACGGAGCCCGAGGATCTAAAACGGGTCCAACAGAACTCGCCGAAGTCGTTGGACTTGACGACGAGTTGAAGAATCCGACAT   4050
 L  L  R  S  P  E  D  L  K  R  V  Q  Q  E  L  A  E  V  V  G  L  D  R  R  V  E  E  S  D  I
CGAGAAGTTGACTTATCTCAAATGCACACTCAAAGGATGCACCCTAAGGATGCACCACGATCCCTCCTCCCACGAAACCGCGGAGGA    4140
 E  K  L  T  Y  L  K  C  T  L  K  E  T  L  R  M  H  P  P  I  P  L  L  H  E  T  A  E  D
CACTAGTATCGACGTTTCTTCATTCCCAAGAGAAATCTCGTGTGATGATCAACGCGTTTGCCATAGGACGGCAATCCAACCTCTTGGACTGA  4230
 T  S  I  D  G  F  F  I  P  K  K  S  R  V  M  I  N  A  F  A  I  G  R  D  P  T  S  W  T  D
CCCGGACACGTTTAGACCATCGAGGTTTTTGGAACCGATTTCAAAGGGAGCAATTTCGAGTTTATACCGTTCGGGTCGGG            4320
 P  D  T  F  R  P  S  R  F  L  E  P  G  V  P  D  F  K  G  S  N  F  E  F  I  P  F  G  S  G
TCGTAGATCGTGCCCGGGTATGCAACTAGGGTTATACGCGTTGACTTAGCGTGGCTCATATATTACATTGCTTCACGTGGAAATTACC    4410
 R  R  S  C  P  G  M  Q  L  G  L  Y  A  L  D  L  A  V  A  H  I  L  H  C  F  T  W  K  L  P
TGATGGGATGAAACCAAGTGAGCTCGACATGAATGATGTGTTTGGTCTCCTAAAGCCACGCGGCTTTTCGCCGTGCCAACCAC         4500
 *  M  G  M  K  P  S  E  L  D  M  N  D  V  F  G  L  T  A  P  K  A  T  R  L  F  A  V  P  T  T
GCGCCTCATCTGTGCTCTTAAGTTTATGGTTCGAGTCACGTGGCAGGGGTTTGGTATGGTGAAAACTGAAAAGTTGAAGTTGCCCTC     4590
 D  G  M  K  P  S  E  L  D  M  N  D  V  F  G  L  T  A  P  K  A  T  R  L  F  A  V  P  T  T
ATCGAGGATTGTGATGTCATATGTATGTATACACGTGTCTTCTGATGAAAACAGATTTGGCTCTTGTTGCCCTTTTTTT            4680
 R  L  I  C  A  L  *
TTTTCTTTAATGGGGATTTCCTTGAATGAAATGTAACAGTAAAAATAAGATTTTTTCAATAAGTAATTTAGCATGTTGCaaagatcg    4770
```

Figure 8D

```
atcttggatgagaacttctactaaaaaaaaaaaaattttttagttatttcacctttttcttttgttctggttgtatggttgcc  4860
attgtcaattaggggctggaagttcgctggttaaatcagagctaaagttataatttacaagcccaacaaaaggtcgcagat  4950
taaaccacacatgatatttataaaaaaattctaaggttttatttattcagttagttttatttcagttactgagtactattactttttatttttt  5040
gcaaataaatgtatttatcatatttatgtttttttgttataaactccaaacatacaggtttcattacctaaaaaaracagagtggtttk  5130
gttaattttgtttcattaatctcgag                                                                 5220
```

Figure 8D

METHOD FOR REGULATION OF PLANT LIGNIN COMPOSITION

This Application is the National Stage of International Application No. PCT/US96/20094, filed Dec. 19, 1996, which claims the benefit of U.S. Provisional application Ser. No. 60/013,388, filed Mar. 14, 1996, and U.S. Provisional Application Ser. No. 60/009,119, filed Dec. 22, 1995. +gi This invention was made with Government support under Contract No. DE-FG02-94ER20138 awarded by the Department of Energy. The Government has certain rights in this invention.

FIELD OF THE INVENTION

The present method relates to the field of molecular biology and the regulation of protein synthesis through the introduction of foreign genes into plant genomes. More specifically, the method relates to the modification of plant lignin composition in a plant cell by the introduction of a foreign plant gene encoding an active ferulate-5-hydroxylase (F5H) enzyme. Plant transformants harboring the F5H gene demonstrate increased levels of syringyl monomer residues in their lignin, a trait that is thought to render the polymer more susceptible to delignification.

BACKGROUND

Lignin is one of the major products of the general phenylpropanoid pathway, and is one of the most abundant organic molecules in the biosphere (Crawford, (1981) *Lignin Biodegradation and Transformation,* New York: John Wiley and Sons). In nature, lignification provides rigidity to wood and is in large part responsible for the structural integrity of plant tracheary elements. Lignin is well suited to these capacities because of its physical characteristics and its resistance to biochemical degradation. Unfortunately, this same resistance to degradation has a significant impact on the utilization of lignocellulosic plant material (Whetten et al., *Forest Ecol. Management* 43, 301, (1991)).

The monomeric composition of lignin has significant effects on its chemical degradation during industrial pulping (Chiang et al., *Tappi,* 71, 173, (1988). The guaiacyl lignins (derived from ferulic acid) characteristic of softwoods such as pine, require substantially more alkali and longer incubations during pulping in comparison to the guaiacyl-syringyl lignins (derived from ferulic acid and sinapic acid) found in hardwoods such as oak. The reasons for the differences between these two lignin types has been explored by measuring the degradation of model compounds such as guaiacylglycerol-β-guaiacyl ether, syringylglycerol-β-guaiacyl ether, and syringylglycerol-β-(4-methylsyringyl) ether (Kondo et al., *Holzforschung,* 41, 83, (1987)) under conditions that mimic those used in the pulping process. In these experiments, the mono- and especially di-syringyl compounds were cleaved three to fifteen times faster than their corresponding diguaiacyl homologues. These model studies are in agreement with studies comparing the pulping of Douglas fir and sweetgum wood where the major differences in the rate of pulping occurred above 150° C. where arylglycerol-β-aryl ether linkages were cleaved (Chiang et al., *Holzforschung,* 44, 309, (1990)).

Another factor affecting chemical degradation of the two lignin forms may be the condensation of lignin-derived guaiacyl and syringyl residues to form diphenylmethane units. The presence of syringyl residues in hardwood lignins leads to the formation of syringyl-containing diphenylmethane derivatives that remain soluble during pulping, while the diphenylmethane units produced during softwood pulping are alkali-insoluble and thus remain associated with the cellulosic products (Chiang et al., *Holzforschung,* 44, 147, (1990); Chiang et al., *Holzforschung,* 44, 309, (1990)). Further, it is thought that the abundance of 5-5'-diaryl crosslinks that can occur between guaiacyl residues contributes to resistance to chemical degradation. This linkage is resistant to alkali cleavage and is much less common in lignin that is rich in syringyl residues because of the presence of the 5-O-methyl group in syringyl residues. The incorporation of syringyl residues results in what is known as "non-condensed lignin", a material that is significantly easier to pulp than condensed lignin.

Similarly, lignin composition and content in grasses is a major factor in determining the digestibility of lignocellulosic materials that are fed to livestock (Jung, H. G. & Deetz, D. A. (1993) Cell wall lignification and degradability in Forage Cell Wall Structure and Digestibility (H. G. Jung, D. R. Buxton, R. D. Hatfield, and J. Ralph eds.), ASA/CSSA/SSSA Press, Madison, Wis.). The incorporation of the lignin polymer into the plant cell wall prevents microbial enzymes from having access to the cell wall polysaccharides that make up the wall. As a result, these polysaccharides cannot be degraded and much of the valuable carbohydrates contained within animal feedstocks pass through the animals undigested. Thus, an increase in the dry matter of grasses over the growing season is counteracted by a decrease in digestibility caused principally by increased cell wall lignification. From these examples, it is clear that the modification of lignin monomer composition would be economically advantageous.

The problem to be overcome, therefore, is to develop a method for the creation of plants with increased levels of syringyl residues in their lignin to facilitate its chemical degradation. Modification of the enzyme pathway responsible for the production of lignin monomers provides one possible route to solving this problem.

The mechanism(s) by which plants control lignin monomer composition has been the subject of much speculation. As mentioned earlier, gymnosperms do not synthesize appreciable amounts of syringyl lignin. In angiosperms, syringyl lignin deposition is developmentally regulated: primary xylem contains guaiacyl lignin, while the lignin of secondary xylem and sclerenchyma is guaiacyl-syringyl lignin (Venverloo, *Holzforschung* 25, 18 (1971); Chapple et al., *Plant Cell* 4, 1413, (1992)). No plants have been found to contain purely syringyl lignin. It is still not clear how this specificity is controlled; however, at least five possible enzymatic control sites exist, namely caffeic acid/5-hydroxyferulic acid O-methyltransferase (OMT), F5H, (hydroxy)cinnamoyl-CoA ligase (4CL), (hydroxy)cinnamoyl-CoA reductase (CCR), and (hydroxy)cinnamoyl alcohol dehydrogenase (CAD). For example, the substrate specificities of OMT (Shimada et al., *Phytochemistry,* 22, 2657, (1972); Shimada et al., *Phytochemistry,* 12, 2873, (1973); Gowri et al., *Plant Physiol,* 97, 7, (1991); Bugos et al., *Plant Mol. Biol.* 17, 1203, (1992)) and CAD (Sarni et al., *Eur. J Biochem.,* 139, 259, (1984); Goffner et al., *Planta.,* 188, 48, (1992); O'Malley et al., *Plant Physiol.,* 98, 1364, (1992)) are correlated with the differences in lignin monomer composition seen in gymnosperms and angiosperms, and the expression of 4CL isozymes (Grand et al., *Physiol. Veg.* 17, 433, (1979); Grand et al., *Planta.,* 158, 225, (1983)) has been suggested to be related to the tissue specificity of lignin monomer composition seen in angiosperms.

Although there are at least five possible enzyme targets that could be exploited, only OMT and CAD have been investigated in recent attempts to manipulate lignin monomer composition in transgenic plants (Dwivedi et al., *Plant Mol. Biol.* 26, 61, (1994); Halpin et al., *Plant J* 6, 339, (1994); Ni et al., *Transgen. Res.* 3, 120 (1994); Atanassova et al., *Plant J.* 8, 465, (1995); Doorsselaere et al., *Plant J* 8, 855, (1995)). Most of these studies have focused on sense and antisense suppression of OMT expression. This approach has met with variable results, probably owing to the degree of OMT suppression achieved in the various studies. The most dramatic effects were seen by using homologous OMT constructs to suppress OMT expression in tobacco (Atanassova et al., supra) and poplar (Doorsselaere et al., supra). Both of these studies found that as a result of transgene expression, there was a decrease in the content of syringyl lignin and a concomitant appearance of 5-hydroxyguaiacyl residues. As a result of these studies, Doorsselaere et al., (WO 9305160) disclose a method for the regulation of lignin biosynthesis through the genomic incorporation of an OMT gene in either the sense or anti-sense orientation. In contrast, Dixon et al. (WO 9423044) demonstrate the reduction of lignin content in plants transformed with an OMT gene, rather than a change in lignin monomer composition. Similar research has focused on the suppression of CAD expression. The conversion of coniferaldehyde and sinapaldehyde to their corresponding alcohols in transgenic tobacco plants has been modified with the incorporation of an *A. cordata* CAD gene in anti-sense orientation (Hibino et al., *Biosci. Biotechnol. Biochem.*, 59, 929, (1995)). A similar effort aimed at antisense inhibition of CAD expression generated a lignin with increased aldehyde content, but only a modest change in lignin monomer composition (Halpin et al., supra). This research has resulted in the disclosure of methods for the reduction of CAD activity using sense and anti-sense expression of a cloned CAD gene to effect inhibition of endogenous CAD expression in tobacco [Boudet et al., (U.S. Pat. No. 5,451,514) and Walter et al., (WO 9324638); Bridges et al., (CA 2005597)]. None of these strategies increased the syringyl content of lignin, a trait that is correlated with improved digestibility and chemical degradability of lignocellulosic material (Chiang et al., supra; Chiang and Funaoka, *Holzforschung* 44, 309 (1990); Jung et al., supra).

Although F5H is also a key enzyme in the biosynthesis of syringyl lignin monomers it has not been exploited to date in efforts to engineer lignin quality. In fact, since the time of its discovery over 30 years ago (Higuchi et al., *Can. J Biochem. Physiol.*, 41, 613, (1963)) there has been only one demonstration of the activity of F5H published (Grand, C., *FEBS Lett.* 169, 7, (1984)). Grand demonstrated that F5H from poplar was a cytochrome P450-dependent monooxygenase (P450) as analyzed by the classical criteria of dependence on NADPH and light-reversible inhibition by carbon monoxide. Grand further demonstrated that F5H is associated with the endoplasmic reticulum of the cell. The lack of attention given to F5H in recent years may be attributed in general to the difficulties associated with dealing with membrane-bound enzymes, and specifically to the lability of F5H when treated with the detergents necessary for solubilization (Grand, supra). The most recent discovery surrounding the F5H gene has been made by Chapple et al., (supra) who reported a mutant of *Arabidopsis thaliana* L. Heynh named fah1 that is deficient in the accumulation of sinapic acid-derived metabolites, including the guaiacyl-syringyl lignin typical of angiosperms. This locus, termed FAH1, encodes F5H. The cloning of the gene encoding F5H would provide the opportunity to test the hypothesis that F5H is a useful target for the engineering of lignin monomer composition.

In spite of sparse information about F5H in the published literature, Applicant has been successful in the isolation, cloning, and sequencing of the F5H gene. Applicant has also demonstrated that the stable integration of the F5H gene into the plant genome, where the expression of the F5H gene is under the control of a promoter other than the gene's endogenous promoter, leads to an altered regulation of lignin biosynthesis.

SUMMARY OF THE INVENTION

The present invention provides isolated nucleic-acid fragments comprising the nucleotide sequences which correspond to SEQ ID NO.: 1 and SEQ ID NO.: 3 encoding an active plant F5H enzyme wherein the enzyme has the amino acid sequence encoded by the mature functional protein which corresponds to SEQ ID NO.: 2 and wherein the amino acid sequence encompasses amino acid substitutions, additions and deletions that do not alter the function of the F5H enzyme.

The invention further provides a chimeric gene causing altered guaiacyl:syringyl lignin monomer ratios in a transformed plant, the gene comprising a nucleic acid fragment encoding an active plant F5H enzyme operably linked in either sense or antisense orientation to suitable regulatory sequences. The nucleic acid fragments are those described above.

Also provided is a method of altering the activity of F5H in a plant by means of transforming plant cells in a whole plant with a chimeric gene causing altered guaiacyl:syringyl lignin monomer ratios in a transformed plant cell, wherein the gene is expressed; growing said plants under conditions that permit seed development; and screening the plants derived from these transformed seeds for those that express an active F5H gene or fragment thereof.

A method is propvided of altering the activity of F5H enzyme in a plant by (i) transforming a cell, tissue or organ from a suitable host plant with the chimeric gene desribed above wherein the chimeric gene is expressed; (ii) selecting transformed cells, cell callus, somatic embryos, or seeds which contain the chimeric gene; (iii) regenerating whole plants from the transformed cells, cell callus, somatic embryos, or seeds selected in step (ii); (iv) selecting whole plants regenerated in step (iii) which have a phenotype characterized by (1) an ability of the whole plant to accumulate compounds derived from sinapic acid or (2) an altered syringyl lignin monomer content relative to an untransformed host plant.

The invention additionally provides a method of altering the composition of lignin in a plant by means of stably incorporating into the genome of the host plant by transformation a chimeric gene causing altered guaiacyl:syringyl lignin monomer ratios in a transformed plant; expressing the incorporated gene such that F5H is expressed and wherein guaiacyl:syringyl lignin monomer ratios are altered from those ratios of the untransformed host plant.

BRIEF DESCRIPTION OF THE FIGURES AN SEQUENCE LISTING

Figure 1:
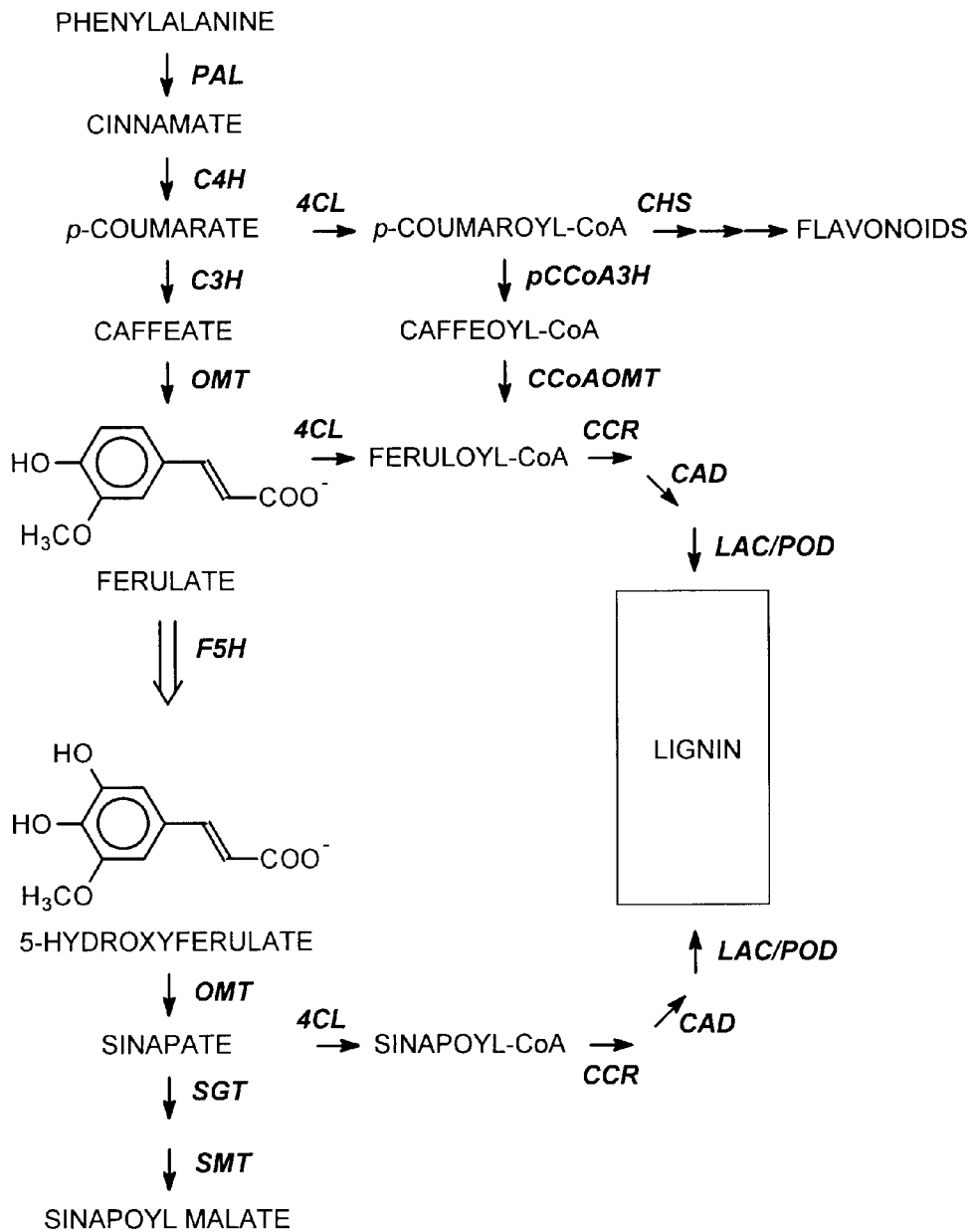
FIG. 1 illustrates the biosynthesis of monomeric lignin precursors via the general phenylpropanoid pathway.

Applicant(s) have provided three sequence listings in conformity with 37 C.F.R. 1.821–1.825 and Appendices A and B ("Requirements for Application Disclosures Containing Nucleotides and/or Amino Acid Sequences") and in conformity with "Rules for the Standard Representation of Nucleotide and Amino Acid Sequences in Patent Applications" and Annexes I and II to the Decision of the President of the EPO, published in Supplement No 2. to OJ EPO, 12/1992.

The sequence of the Arabidopsis thaliana F5H cDNA is given in SEQ ID NO.: 1 and the sequence of the Arabidopsis thaliana F5H genomic clone is given in SEQ ID NO.: 3. The sequence of the F5H protein is given in SEQ ID NO.: 2.

DETAILED DESCRIPTION OF THE INVENTION

The present invention provides a gene that encodes F5H, a key enzyme in lignin biosynthesis. The invention further provides a method for altering the lignin composition in plants by transforming plants with the F5H gene wherein the gene is expressed and causes an increased conversion of ferulic acid to sinapic acid thereby increasing the syringyl content of the lignin polymer.

The effect in plants of lignin compositions containing higher syringyl monomer content is that the lignin is more susceptible to chemical delignification. This is of particular use in the paper and pulp industries where vast amounts of energy and time are consumed in the delignification process. Woody plants transformed with an active F5H gene would offer a significant advantage in the delignification process over conventional paper feedstocks. Similarly, modification of the lignin composition in grasses by the insertion and expression of a heterologus F5H gene offers a unique method for increasing the digestibility of livestock feed. Maximizing the digestibility of grasses in this manner offers great potential economic benefit to the farm and agricultural industries.

Plants to which the Invention may be Applied

The invention provides a gene and a chimeric gene construct useful for the transformation of plant tissue for the alteration of lignin monomer composition. Plants suitable in the present invention comprise plants that naturally lack syringyl lignin or those that accumulate lignin with a high guaiacyl:syringyl ratio. Plants suitable in the present invention also comprise plants whose lignin could be modified using antisense transformation constructs that reduce the syringyl content of the transgenic plants' lignin if such an alteration were desirable.

Suitable plants may include but are not limited to alfalfa (Medicago sp.), rice (Oryza sp.), maize (Zea mays), oil seed rape (Brassica sp.), forage grasses, and also tree crops such as eucalyptus (Eucalyptus sp.), pine (Pinus sp.), spruce (Picea sp.) and poplar (Populus sp.), as well as Arabidopsis sp. and tobacco (Nicotiana sp).

Definitions

As used herein the following terms may be used for interpretation of the claims and specification.

The term "FAH1" refers to the locus or chromosomal location at which the F5H gene is encoded. The term "FAH1" refers to the wild type allele of the gene encoding the F5H gene. The term "fah1" refers to any mutant version of that gene that leads to an altered level of enzyme activity, syringyl lignin content or sinapate ester content that can be measured by thin layer chromatography, high performance liquid chromatography, or by in vivo fluorescence.

"Gene" refers to a nucleic acid fragment that expresses a specific protein, including regulatory sequences preceding (5' non-coding) and following (3' non-coding) the coding region. "Native" gene refers to the gene as found in nature with its own regulatory sequences.

A "chimeric gene" refers to a gene comprising heterogeneous regulatory and coding sequences.

An "endogenous gene" refers to the native gene normally found in its natural location in the genome.

A "foreign gene" or "transgene" refers to a gene not normally found in the host organism but one that is introduced by gene transfer.

The term "promoter" refers to a DNA sequence in a gene, usually upstream (5') to its coding sequence, which controls the expression of the coding sequence by providing the recognition site for RNA polymerase and other factors required for proper transcription. A promoter may also contain DNA sequences that are involved in the binding of protein factors which control the effectiveness of transcription initiation in response to physiological or developmental conditions.

The term "operably linked" refers to nucleic acid sequences on a single nucleic acid molecule which are associated so that the function of one is affected by the other.

As used herein, suitable "regulatory sequences" refer to nucleotide sequences located upstream (5'), within, and/or downstream (3') of a coding sequence, which control the transcription and/or expression of the coding sequences in conjunction with the protein biosynthetic apparatus of the cell. These regulatory sequences include promoters, translation leader sequences, transcription termination sequences, and polyadenylation sequences.

The term "T-DNA" refers to the DNA that is transferred into the plant genome from a T-DNA plasmid carried by a strain of Agrobacterium tumefaciens that is used to infect plants for the purposes of plant transformation.

The term "T-DNA plasmid" refers to a plasmid carried by Agrobacteriurn tumefaciens that carries an origin of replication, selectable markers such as antibiotic resistance, and DNA sequences referred to as right and left borders that are required for plant transformation. The DNA sequence that is transferred during this process is that which is located between the right and left T-DNA border sequences present on a T-DNA plasmid. The DNA between these borders can be manipulated in such a way that any desired sequence can be inserted into the plant genome.

The term "ferulate-5-hydroxylase" or "F5H" will refer to an enzyme in the plant phenylpropanoid biosynthetic pathway which catalyzes the conversion of ferulate to 5-hydroxyferulate and permits the production of sinapic acid and its subsequent metabolites, including sinapoylmalate and syringyl lignin.

The terms "encoding" and "coding" refer to the process by which a gene, through the mechanisms of transcription and translation, provides the information to a cell from which a series of amino acids can be assembled into a specific amino acid sequence to produce an active enzyme. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (2X SSC, 0.1% SDS, 65° C.), with the sequences exemplified herein.

The term "expression", as used herein, refers to the production of the protein product encoded by a gene. "Overexpression" refers to the production of a gene product in transgenic organisms that exceeds levels of production in normal or non-transformed organisms.

"Transformation" refers to the transfer of a foreign gene into the genome of a host organism and its genetically stable inheritance. Examples of methods of plant transformation include Agrobacterium-mediated transformation and particle-accelerated or "gene gun" transformation technology as described in U.S. Pat. No. 5,204,253.

The term "plasmid rescue" will refer to a technique for circularizing restriction enzyme-digested plant genomic DNA that carries T-DNA fragments bearing a bacterial origin of replication and antibiotic resistance (encoded by the β-lactamase gene of E. coli) such that this circularized fragment can be propagated as a plasmid in a bacterial host cell such as E. coli.

The term "lignin monomer composition" refers to the relative ratios of guaiacyl monomer and syringyl monomer found in lignified plant tissue.

The Phenylpropanoid Biosynthetic Pathway

The lignin biosynthetic pathway is well researched and the principal pathways are illustrated in FIG. 1. Lignin biosynthesis is initiated by the conversion of phenylalanine into cinnamate through the action of phenylalanine ammonia lyase (PAL). The second enzyme of the pathway is cinnamate-4-hydroxylase (C4H), a cytochrome P450-dependent monooxygenase (P450) which is responsible for the conversion of cinnamate to p-coumarate. The second hydroxylation of the pathway is catalyzed by a relatively ill-characterized enzyme, p-coumarate-3-hydroxylase (C3H), whose product is caffeic acid. Caffeic acid is subsequently O-methylated by OMT to form ferulic acid, a direct precursor of lignin. The last hydroxylation reaction of the general phenylpropanoid pathway is catalyzed by F5H. The 5-hydroxyferulate produced by F5H is then O-methylated by OMT, the same enzyme that carries out the O-methylation of caffeic acid. This dual specificity of OMT has been confirmed by the cloning of the OMT gene, and expression of the protein in E. coli (Bugos et al., (1991) supra; Gowri et al., (1991) supra).

The committed steps of lignin biosynthesis are catalyzed by 4CL, (hydroxy)cinnamoyl CoA reductase (CCR) and CAD, which ultimately generate coniferyl alcohol from ferulic acid and sinapoyl alcohol from sinapic acid. Coniferyl alcohol and sinapoyl alcohol are polymerized by extracellular oxidases to yield guaiacyl lignin and syringyl lignin respectively, although syringyl lignin is more accurately described as a co-polymer of both monomers.

Figure 5:
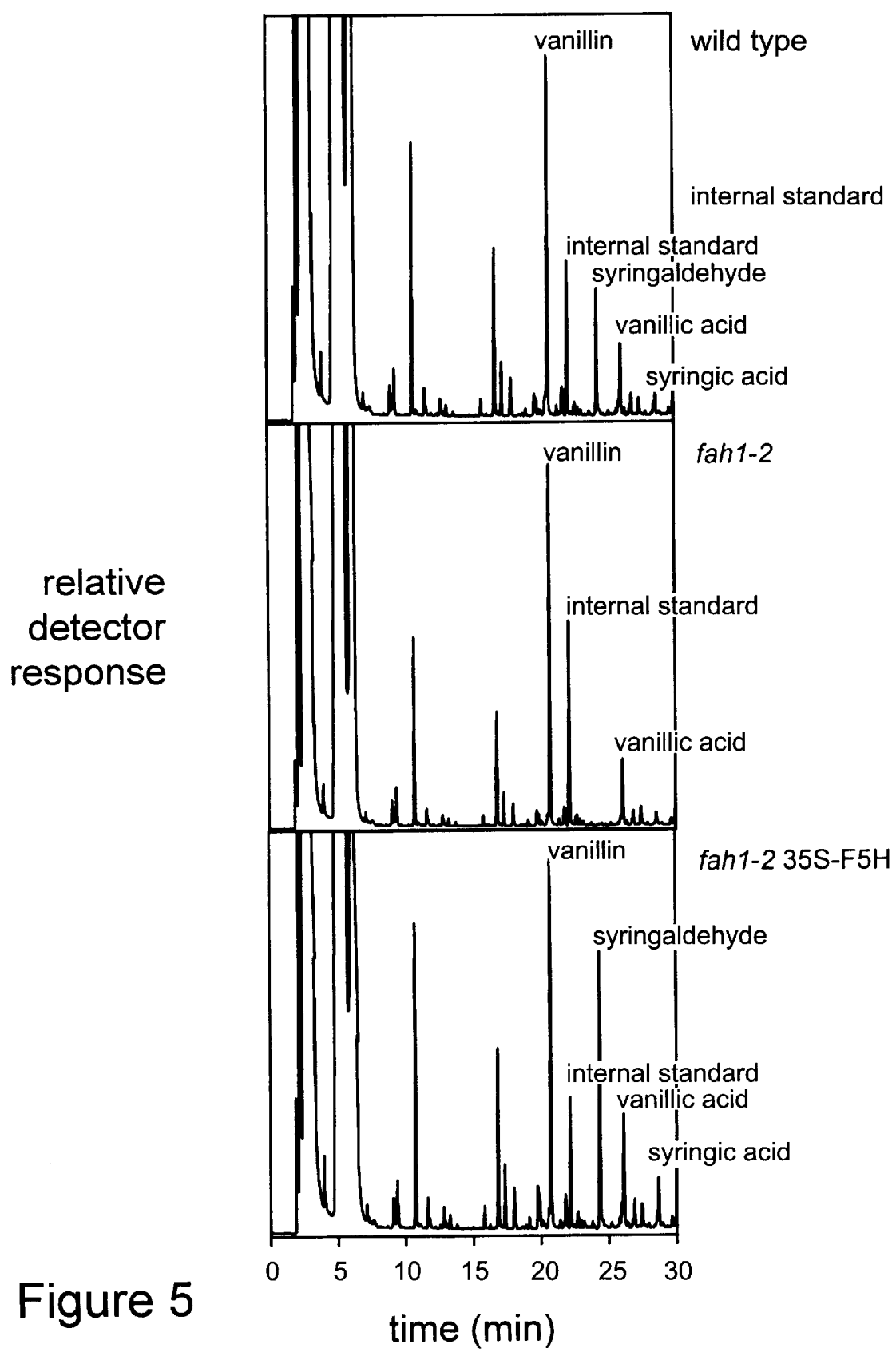
FIG. 5 shows a GC analysis of lignin nitrobenzene oxidation products to illustrate the impact of F5H overexpression on lignin monomer composition in the wild type, the fah1-2 mutant, and a fah1-2 mutant carrying the T-DNA derived from the 35S-F5H overexpression construct.

Although ferulic acid, sinapic acid, and in some cases p-coumaric acid are channeled into lignin biosynthesis, in some plants these compounds are precursors for other secondary metabolites. In Arabidopsis, sinapic acid serves as a precursor for lignin biosynthesis but it is also channeled into the synthesis of soluble sinapic acid esters. In this pathway, sinapic acid is converted to sinapoylglucose which serves as an intermediate in the biosynthesis of sinapoylmalate (FIG. 5). Sinapic acid and its esters are fluorescent and may be use as a marker of plants deficient in those enzymes needed to produce sinapic acid (Chapple et al., supra).

Identification of the FAH1 Locus and fah1 Alleles

A series of mutants of Arabidopsis that fail to accumulate sinapoylmalate have been identified and have been collectively termed fah1 mutants. The fluorescent nature of sinapoylmalate permits the facile identification of sinapic acid esters by thin layer chromatography (TLC) followed by observation under ultraviolet (UV) light). The fluorescence of sinapoylmalate can also be visualized in vivo because sinapoylmalate is accumulated in the adaxial leaf epidermis. Wild type Arabidopsis exhibits a pale blue fluorescence under UV while fah1 mutants appear dark red because of the lack of the blue fluorescence of sinapoylmalate and the fluorescence of chlorophyll in the subtending mesophyll (Chapple et al., supra).

A TLC-based mutant screen of 4,200 ethyl methanesulfonate-mutagenized Arabidopsis plants identified a number of independent mutant lines that accumulated significantly lower levels of sinapoylmalate. The mutations in these lines were identified as fah1—1 through fah1–5. The in vivo UV-fluorescence visual screen was used to identify more mutant lines carrying the fah1 mutation. Two of these mutants (fah1–6 and fah1–7) were selected from EMS-mutagenized populations. One mutant line (fah1–8) was selected from among a mutant population generated by fast-neutron bombardment (Nilan, R. A. *Nucl. Sci. Abstr.,* 28(3), 5940 (1973); Kozer et al., *Genet. Pol.,* 26(3),367, (1985)). A final mutant line, (fah1–9) was identified using the same technique from a T-DNA tagged population of plants. Before further analysis, each mutant line was back-crossed at least twice to the wild type and homozygous lines were established.

To determine whether the newly isolated mutant lines were defective at the same locus, that is, within the gene encoding F5H, genetic complementation experiments were performed. In these tests, each mutant line was crossed to fah1–2 which is known to be defective in F5H. In each case, the newly isolated mutant line was used as the female parent and was fertilized with pollen from a fah1–2 homozygous mutant. A reciprocal cross was also performed using fah1–2 as the female parent, and the new mutant line as the pollen donor. The seeds from these crosses were collected several weeks later, and were planted for subsequent analysis. The progeny were analyzed for sinapoylmalate production by TLC, high pressure liquid chromatography and by observation under UV light. From these crosses, all of the F1 progeny examined were sinapoylmalate-deficient, indicating that all of the mutations identified were allelic.

The fah1–9 line was selected for further study because of the presence of the T-DNA insertion within the F5H gene. The T-DNA insertion within the FAH1 locus facilitated the cloning of the flanking Arabidopsis DNA which could then be used to retrieve the wild type F5H gene from cDNA and genomic libraries (Meyer et al., *Proc. Natl. Acad. Sci. USA,* 93, 6869 (1996)).

Cloning of the FAH1 Locus

A fragment of DNA from the FAH1 locus was isolated from the T-DNA tagged fah1–9 mutant using the technique of plasmid rescue (Meyer et al., supra). The technique of plasmid rescue is common and well known in the art and may be used to isolate specific alleles from T-DNA transformed plants (Behringer, et al., *Plant Mol. Biol. Rep.,* 10, 190,(1992)). Briefly, the vector used to generate the T-DNA tagged population of Arabidopsis carries sequences required for autonomous replication of DNA in bacteria and sequences that confer antibiotic resistance. Once this DNA is integrated into the plant genome, specific restriction endonuclease digests can be employed to generate fragments that can be circularized, ligated, and transformed into *E. coli*. Circularized DNA from the T-DNA will generate functional plasmids that confer antibiotic resistance to their bacterial hosts such that they can be identified by growth on selective media. Those plasmids that are generated from the sequences including the right and left borders will also carry with them the plant genomic sequences flanking the T-DNA insertion. Plasmids generated from either of the T-DNA borders that carry flanking DNA sequences can be identified by analyzing the products of diagnostic restriction enzyme digests on agarose gels. The plasmids with flanking sequences can then serve as a starting point for cloning plant sequences that share homology to the DNA at the point of T-DNA insertion (Behringer, et al., supra).

Plasmid rescue was conducted using EcoRI-digested DNA prepared from homozygous fah1–9 plants. EcoRI-digested genomic DNA was ligated and then electroporated into competent DH5α *E. coli*. DNA from rescued plasmids was further digested with both EcoRI and SalI and the digests were analyzed by gel electrophoresis to identify plasmids that contained flanking Arabidopsis DNA. A SacII-EcoRI fragment from this rescued plasmid was used to identify an F5H clone from an Arabidopsis cDNA library (Newman, T. et al., *Plant. Physiol.* 106, 1241, (1994)).

DNA Sequencing of the F5H cDNA and genomic clones

Sequence analysis of the F5H cDNA and genomic clones was performed on plasmid DNA manually using a United States Biochemical Sequenase Kit v. 2.0, on a DuPont Genesis® 2000 sequencer or on an Applied Biosystems 373A DNA sequencer, using standard vector-based sequencing oligonucleotides or custom-synthesized oligonucleotides as appropriate. The sequence of the *Arabidopsis thaliana* F5H cDNA is given in SEQ ID NO.: 1 and the sequence of the *Arabidopsis thaliana* F5H genomic clone is given in SEQ ID NO.: 3.

Figure 8A:
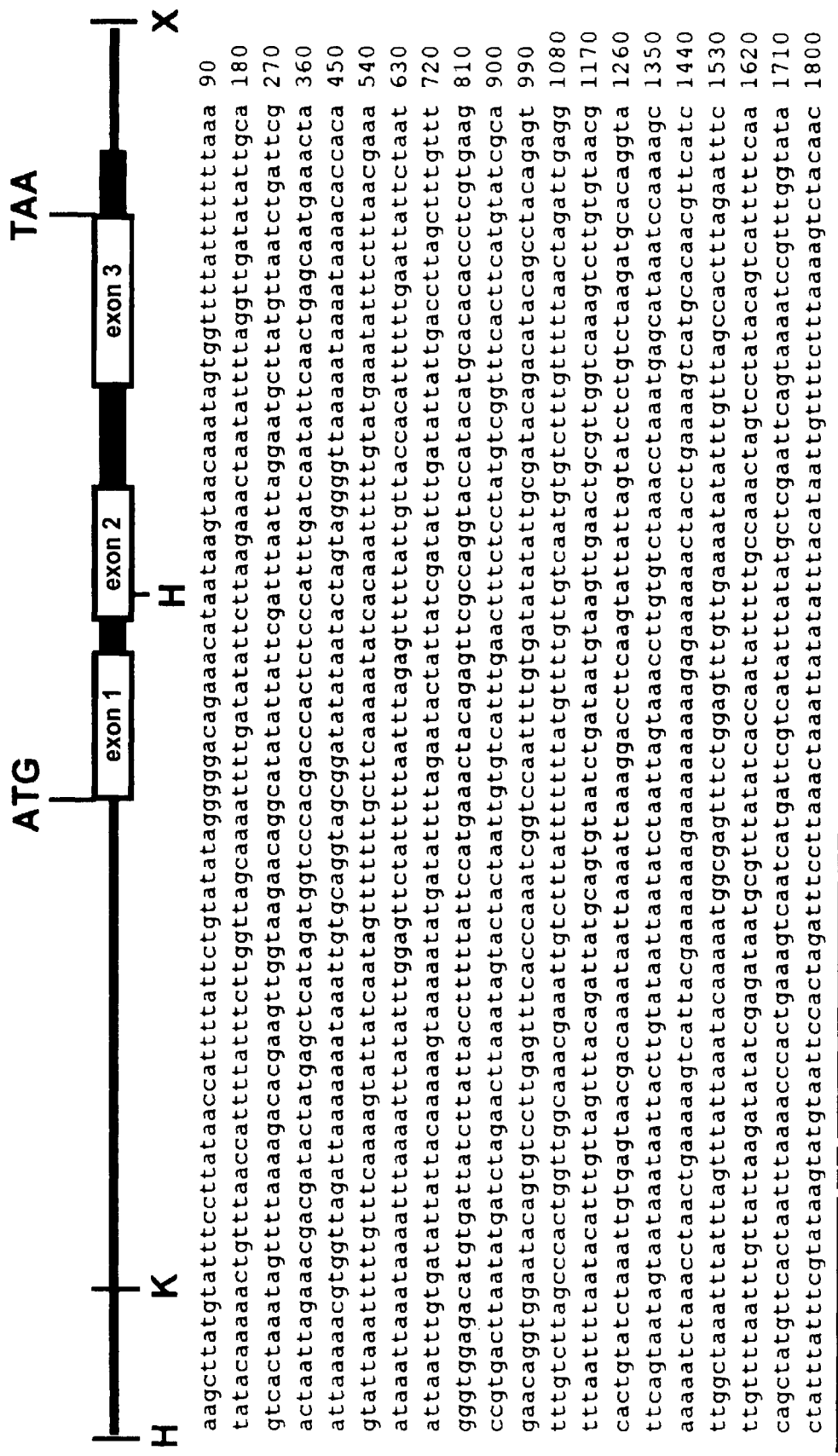
FIG. 8 shows the genomic nucleotide (SEQ ID NO.: 3) and amino acid (SEQ ID NO.: 2) sequences of the Arabidopsis F5H gene and the F5H enzyme that it encodes.

The F5H cDNA contains a 1560 bp open reading frame that encodes a protein with a molecular weight of 58,728. The putative ATG initiation codon is flanked by an A at −3 and a G at +4, in keeping with the nucleotides commonly found flanking the initiator methionine in plant mRNAs (Lutcke et al., *EMBO J* 6, 43, (1987)). Immediately following the inferred initiator methionine is a 17 amino acid sequence containing nine hydroxy amino acids (FIG. 8). The subsequent fifteen amino acid sequence is rich in hydrophobic amino acids; eleven hydrophobic residues comprised of phenylalanine, isoleucine, leucine and valine residues. This hydrophobic stretch is immediately followed by an Arg-Arg-Arg-Arg putative stop transfer sequence. F5H also shares significant sequence identity with other P450s. Most notable is the stretch between Pro-450 and Gly-460. This region contains eight residues that comprise the heme-binding domain and are highly conserved among most P450s, one exception being allene oxide synthase from *Linum usitatissimum* (Song et al., *Proc. Natl. Acad Sci. USA* 90, 8519, (1993)). The Pro-450 to Gly-460 region contains Cys-458 in F5H, which by analogy is most likely the heme binding ligand in this enzyme.

Figure 2:
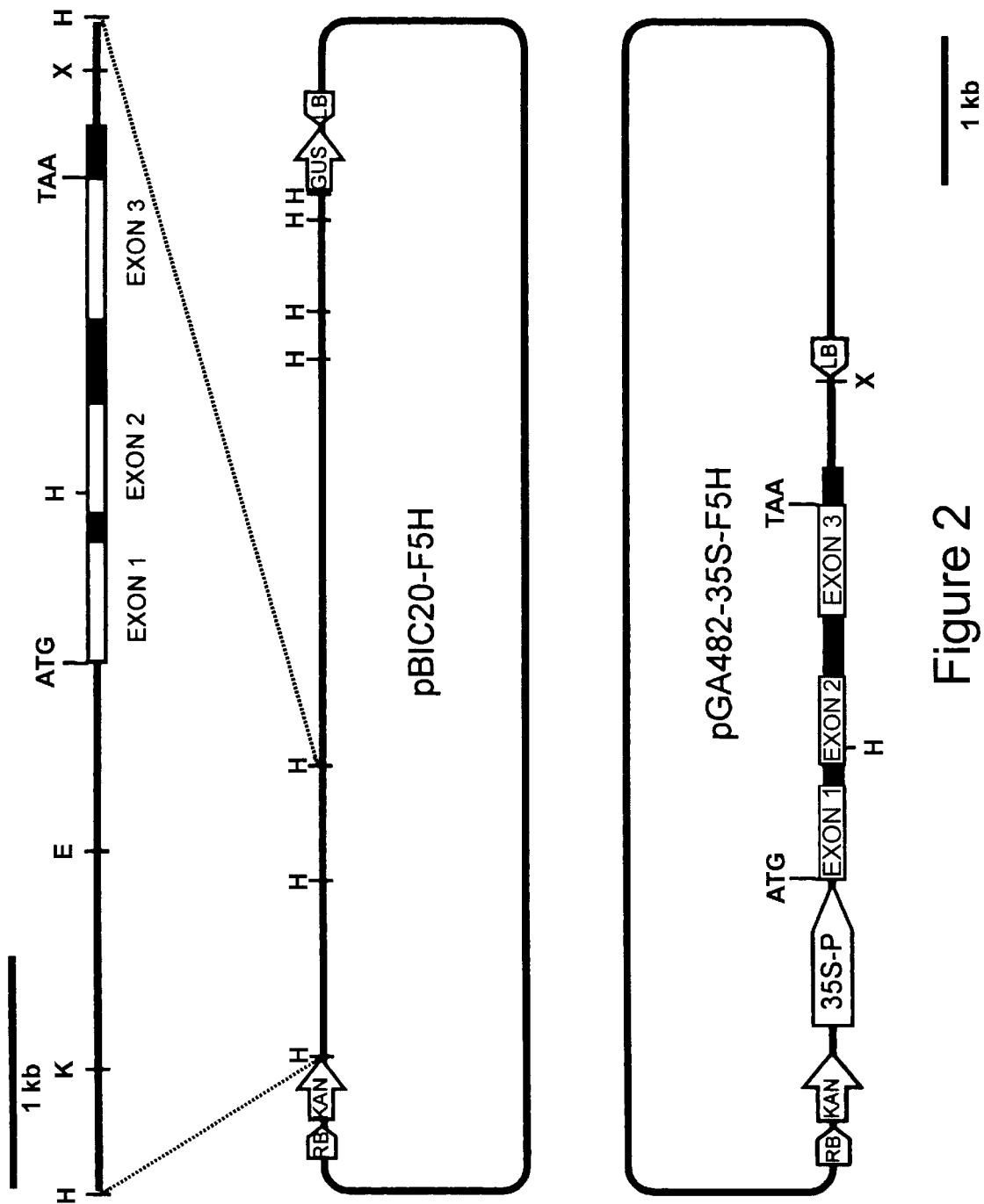
FIG. 2 is an illustration of the pBIC20-F5H cosmid and the F5H overexpression construct (pGA482-35S-F5H) in which the F5H gene is expressed under the control of the constitutive cauliflower mosaic virus 3 5S promoter.
Figure 3:
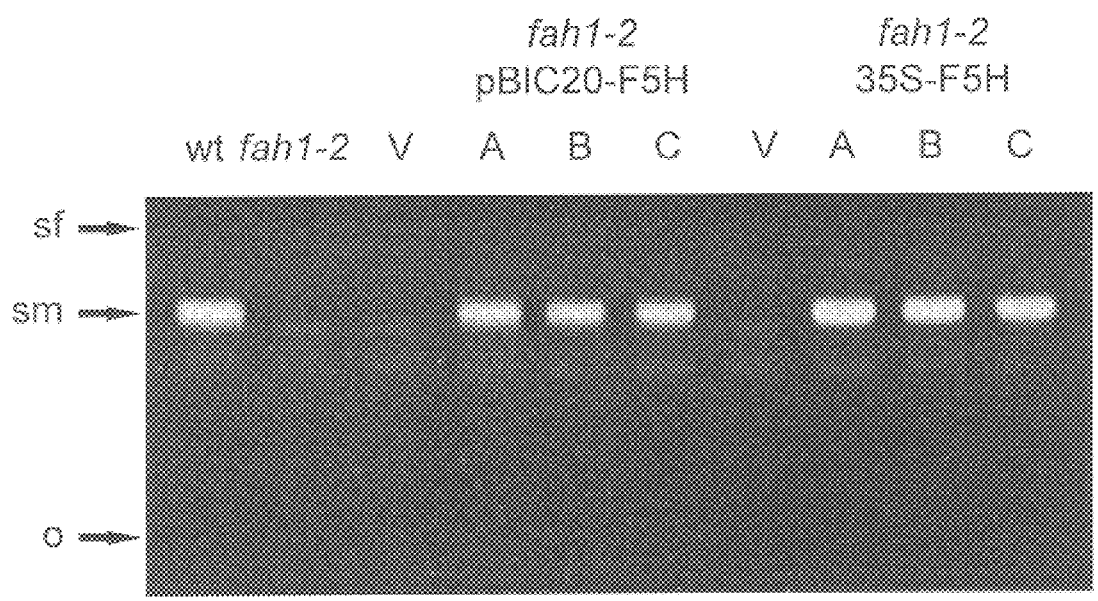
FIG. 3 shows an analysis of sinapic acid-derived secondary metabolites in wild type, the fah1-2 mutant, and independently-derived transgenic fah1-2 plants carrying the T-DNA derived from the pBIC20-F5H cosmid, or the pGA482-35S-F5H overexpression construct.

Transformation of fah1–2 Arabidopsis and Restoration of Sinapoylmalate Accumulation The identity of the F5H gene was confirmed by complementation of the fah1–2 mutant with a genomic clone and a construct where the F5H genomic coding sequence was expressed under the control of the cauliflower mosaic virus 35S promoter. Briefly, the F5H cDNA was used as a probe to screen a transformation competent library (Meyer et al., (1994) *Science,* 264, 1452–1455) for genomic clones. Using this method, a cosmid clone (pBIC20-F5H) was isolated that carried a 17 kb genomic insert containing the inferred start and stop codons of the F5H gene (FIG. 2). The portion of this cosmid carrying the F5H open reading frame was excised from the cosmid and subcloned into a vector in which it was operably linked to the cauliflower mosaic virus 35S promoter (pGA482-35S-F5H) (FIG. 2). Both the original cosmid and this derivative plasmid construct were electroporated into *Agrobacterium tumefaciens* and were used to transform fah1–2 mutants. Success of the transformations was evidenced by TLC assays demonstrating sinapoylmalate accumulation in leaf tissues of the fah1–2 transformants carrying the T-DNA from the pBIC20-F5H cosmid or the pGA482-35S-F5H plasmid (FIG. 3). These data clearly indicated that the gene encoding F5H had been identified.

Modification of Lignin Composition in Plants Transformed With F5H Under the Control of the Cauliflower Mosaic Virus 35S Promoter Arabidopsis plants homozygous for the fah1–2 allele were transformed with Agrobacterium carrying the pGA482-35S-

Figure 4:
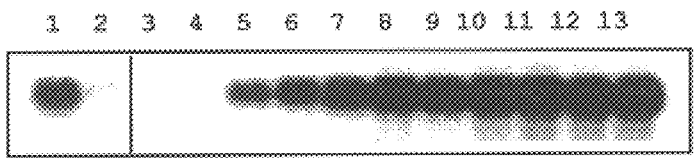
FIG. 4 shows the impact of F5H overexpression by comparing the steady state levels of F5H mRNA in wild type, the fah1-2 mutant, and independently-derived transgenic fah1-2 plants carrying the T-DNA derived from the 35S-F5H overexpression construct.

F5H plasmid which contains the chimeric F5H gene under the control of the constitutive cauliflower mosaic virus 35S promoter (Odell, et al., *Nature* 313, 810–812, (1985)). Independent homozygous transformants carrying the F5H transgene at a single genetic locus were identified by selection on kanamycin-containing growth media, grown up in soil and plant tissue was analyzed for lignin monomer composition. Nitrobenzene oxidation analysis of the lignin in wild type, fah1–2, and transformants carrying the T-DNA from the pGA482-35S-F5H construct revealed that F5H overexpression as measured by northern blot analysis (FIG. 4) led to a significant increase in the transgenic lignin (FIG. 5). The lignin of the F5H-overexpressing plants demonstrated a syringyl content as high as 29 mol % as opposed to the syringyl content of the wild type lignin which was 18 mol % (Table 1) (Example 5). These data clearly demonstrate that overexpression of the F5H gene is useful for the alteration of lignin composition in transgenic plants.

TABLE 1

Impact of 35S Promoter-Driven F5H Expression on Lignin Monomer Composition in Arabidopsis

| Line | mol % S |
| --- | --- |
| wild type | 18.4 +/- 0.91 |
| 88 | 5.06 +/- 0.17 |
| 172 | 13.7 +/- 0.55 |
| 170 | 19.2 +/- 0.56 |
| 122 | 19.9 +/- 0.86 |
| 108 | 22.7 +/- 0.82 |
| 107 | 25.3 +/- 1.23 |
| 180 | 25.8 +/- 0.78 |
| 117 | 28.8 +/- 0.92 |
| 128 | 27.5 +/- 1.80 |

In a similar fashion, T1 tobacco (*Nicotiana tabacum*) F5H transformants were generated, grown up and analyzed for lignin monomer composition. Nitrobenzene oxidation analysis demonstrated that the syringyl monomer content of the leaf midribs was increased from 14 mol % in the wild type to 40 mol % in the transgenic line that most highly expressed the F5H transgene (Table 2).

TABLE 2

Impact of 35S Promoter-Driven F5H Expression on Lignin Monomer Composition in Tobacco Leaf Midrib Xylem

| Line | mol % S |
| --- | --- |
| wild type | 14.3 +/- 1.09 |
| 40 | 22.4 +/- 1.53 |
| 27 | 31.3 +/- 0.50 |
| 48 | 35.7 +/- 6.06 |
| 33 | 40.0 +/- 1.86 |

Construction of Chimeric Genes for the Expression of F5H in Plants.

The expression of foreign genes in plants is well-established (De Blaere et al. (1987) *Meth. Enzymol.* 143:277–291) and this invention provides for a method to apply this technology to the introduction of a chimeric gene for the overexpression of the F5H gene in plants for the manipulation of lignin monomer composition. The expression of the F5H mRNAs at an appropriate level may require the use of different chimeric genes utilizing different promoters. A preferred class of heterologous hosts for the expression of the coding sequence of the F5H gene are eukaryotic hosts, particularly the cells of higher plants. Particularly preferred among the higher plants and the seeds derived from them are alfalfa (Medicago sp.), rice (Oryza sp.), maize (*Zea mays*), oil seed rape (Brassica sp.), forage grasses, and also tree crops such as eucalyptus (Eucalyptus sp.), pine (Pinus sp.), spruce (Picea sp.) and poplar (Populus sp.), as well as Arabidopsis sp. and tobacco (Nicotiana sp.). Expression in plants will use regulatory sequences functional in such plants.

The origin of the promoter chosen to drive the expression of the coding sequence is not critical as long as it has sufficient transcriptional activity to accomplish the invention by expressing translatable mRNA for the F5H gene in the desired host tissue. Preferred promoters will effectively target F5H expression to those tissues that undergo lignification. These promoters may include, but are not limited to promoters of genes encoding enzymes of the phenylpropanoid pathway such as the PAL promoter (Ohl et al., *Plant Cell*, 2, 837, (1990) and the 4CL promoter (Hauffed et al., *Plant Cell*, 3, 435, (1991).

Depending upon the application, it may be desirable to select promoters that are specific for expression in one or more organs of the plant. Examples include the light-inducible promoters of the small subunit of ribulose 1,5-bisphosphate carboxylase, if the expression is desired in photosynthetic organs, or promoters active specifically in roots.

Expression of F5H Chimeric Genes in Plants

Various methods of introducing a DNA sequence (i.e., of transforming) into eukaryotic cells of higher plants are available to those skilled in the art (see EPO publications 0 295 959 A2 and 0 138 341 A1). Such methods include those based on transformation vectors based on the Ti and Ri plasmids of Agrobacterium spp. It is particularly preferred to use the binary type of these vectors. Ti-derived vectors transform a wide variety of higher plants, including monocotyledonous and dicotyledonous plants, such as soybean, cotton, tobacco, Arabidopsis and rape (Pacciotti et al., *Bio/Technology* 3, 241, (1985); Byrne et al., *Plant Cell, Tissue and Organ Culture* 8, 3, (1987); Sukhapinda et al., *Plant Mol Biol.* 8, 209, (1987); Lorz et al., *Mol. Gen. Genet* 199, 178, (1985); Potrykus *Mol. Gen. Genet.* 199, 183, (1985)).

For introduction into plants the chimeric genes of the invention can be inserted into binary vectors as described in Example 5.

Other transformation methods are available to those skilled in the art, such as direct uptake of foreign DNA constructs [see EPO publication 0 295 959 A2], techniques of electroporation [see Fromm et al. (1986) *Nature* (London) 319:791] or high-velocity ballistic bombardment with metal particles coated with the nucleic acid constructs (see Kline et al., *Nature* (London) 327:70 (1987), and see U.S. Pat. No. 4,945,050). Once transformed, the cells can be regenerated by those skilled in the art.

The following Examples are meant to illustrate key embodiments of the invention but should not be construed to be limiting in any way.

EXAMPLES

GENERAL METHODS

Restriction enzyme digestions, phosphorylations, ligations and transformations were done as described in Sambrook et al., Molecular Cloning: A Laboratory Manual, Second Edition (1989) Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "µL" means microliter(s), "mL" means milliliters, "L" means liters, "g" means grams, "mg" means milligrams, "µg" means microgram(s), "nm" means nanometer(s), "m" means meter(s), "E" means Einstein(s).

Plant material

*Arabidopsis thaliana* was grown under a 16 h light/8 h dark photoperiod at 100 mE m$^{-2}$ s$^{-1}$ at 24° C. cultivated in METROMIX 2000 potting mixture (Scotts, Marysville Ohio). Mutant lines fah1-1 through fah1-5 were identified by TLC as described below. Using their red fluorescence under UV light as a marker, mutant lines fah1-6, fah1-7, and fah1-8 were selected from ethylmethane sulfonate (fah1-6, fah1-7) or fast-neutron (fah1-8) mutagenized populations of Landsberg erecta M2 seed. The T-DNA tagged line 3590 (fah1-9) was similarly identified in the DuPont T-DNA tagged population (Feldmann, K. A., Malmberg, R. L., & Dean, C., (1994) *Mutagenesis in Arabidopizs* in Arabidopsis, (E. M. Meyerowitz and C. R. Somerville, eds.) Cold Spring Harbor Press). All lines were backcrossed to wild type at least twice prior to experimental use to remove unlinked background mutations.

Secondary Metabolite Analysis

Leaf extracts were prepared from 100 mg samples of fresh leaf tissue suspended in 1 mL of 50% methanol. Samples were vortexed briefly, then frozen at −70° C. Samples were thawed, vortexed, and centrifuged at 12,000 ×g for 5 min. Sinapoylmalate content was qualitatively determined following silica gel TLC, in a mobile phase of n-butanol/ethanol/water (4:1:1). Sinapic acid and its esters were visualized under long wave UV light (365 nm) by their characteristic fluorescence.

Southern Analysis

For Southern analysis, DNA was extracted from leaf material (Rogers, et al., (1985) *Plant Mol Biol.* 5, 69), digested with restriction endonucleases and transferred to HYBOND N+ membrane (Amersham, Cleveland Ohio) by standard protocols. cDNA probes were radiolabelled with $^{32}$P and hybridized to the target membrane in Denhardt's hybridization buffer (900 mM sodium chloride, 6 mM disodium EDTA, 60 mM sodium phosphate pH 7.4, 0.5% SDS, 0.01% denatured herring sperm DNA and 0.1% each polyvinylpyrrolidone, bovine serum albumin, and FICOLL 400) containing 50% formamide at 42° C. To remove unbound probe, membranes were washed twice at room temperature and twice at 65° C. in 2× SSPE (300 mM sodium chloride, 2 mM disodium EDTA, 20 mM sodium phosphate, pH 7.4) containing 0.1% SDS, and exposed to film.

Northern Analysis

RNA was first extracted from leaf material according to the following protocol.

For extraction of RNA, Covey's extraction buffer was prepared by dissolving 1% (w/v) TIPS (triisopropyl-naphthalene sulfonate, sodium salt), 6% (w/v) PAS (p-aminosalicylate, sodium salt) in 50 mM Tris pH 8.4 containing 5% v/v Kirby's phenol. Kirby's phenol was prepared by neutralizing liquified phenol containing 0.1% (w/v) 8-hydroxyquinoline with 0.1 M Tris-HCl pH 8.8. For each RNA preparation, a 1 g samples of plant tissue was ground in liquid nitrogen and extracted in 5 mL Covey's extraction buffer containing 10 µL β-mercaptoethanol. The sample was extracted with 5 mL of a 1:1 mixture of Kirby's phenol and chloroform, vortexed, and centrifuged for 20 min at 7,000×g. The supernatant was removed and the nucleic acids were precipitated with 500 µL of 3 M sodium acetate and 5 mL isopropanol and collected by centrifugation at 10,000×g for 10 min. The pellet was redissolved in 500 µL water, and the RNA was precipitated on ice with 250 µL 8 M LiCl, and collected by centrifugation at 10,000×g for 10 min. The pellet was resuspended in 200 µL water and extracted with an equal volume of chloroform:isoamyl alcohol 1:1 with vortexing. After centrifugation for 2 min at 10,000 ×g, the upper aqueous phase was removed, and the nucleic acids were precipitated at −20° C. by the addition of 20 µL 3 M sodium acetate and 200 µL isopropanol. The pellet was washed with 1 mL cold 70% ethanol, dried, and resuspended in 100 µL water. RNA content was assayed spectrophotometrically at 260 nm. Samples containing 1 to 10 µg of RNA were subjected to denaturing gel electrophoresis as described elsewhere (Sambrook et al., supra).

Extracted RNA was transferred to HYBOND N$^+$ membrane (Amersham, Cleveland Ohio), and probed with radiolabelled probes prepared from cDNA clones. Blots were hybridized overnight, washed twice at room temperature and once at 65° C. in 3× SSC (450 mM sodium chloride, 45 mM sodium citrate, pH 7.0) containing 0.1% SDS, and exposed to film.

Identification of cDNA and Genomic Clones cDNA and genomic clones for F5H were identified by standard techniques using a 2.3 kb SacII/EcoRI fragment from the rescued plasmid (pCC1) (Example 2) as a probe. The cDNA clone pCC30 was identified in the λPRL2 library (Newman et al., (1994) supra) kindly provided by Dr. Thomas Newman (DOE Plant Research Laboratory, Michigan State University, East Lansing, Mich.). A genomic cosmid library of *Arabidopsis thaliana* (ecotype Landsberg erecta) generated in the binary cosmid vector pBIC20 (Example 3) (Meyer et al., *Science* 264, 1452, (1994)) was screened with the radiolabelled cDNA insert derived from pCC30. Genomic inserts in the pBIC20 T-DNA are flanked by the neomycin phosphotransferase gene for kanamycin selection adjacent to the T-DNA right border sequence, and the β-glucuronidase gene for histochemical selection adjacent to the left border. Positive clones were characterized by restriction digestion and Southern analysis in comparison to Arabidopsis genomic DNA.

Plant transformation

Transformation of *Arabidopsis thaliana* was performed by vacuum infiltration (Bent et al., *Science* 265, 1856, (1994)) with minor modifications. Briefly, 500 mL cultures of transformed Agrobacterium harboring the pBIC20-F5H cosmid or the pGA482-35S-F5H construct were grown to stationary phase in Luria broth containing 10 mg L$^{-1}$ rifampicin and 50 mg L$^{-1}$ kanamycin. Cells were harvested by centrifugation and resuspended in 1 L infiltration media containing 2.2 g MS salts (Murashige and Skoog, *Physiol. Plant.* 15, 473, (1962)), Gamborg's B5 vitamins (Gamborg et al., *Exp. Cell Res.* 50, 151, (1968)), 0.5 g MES, 50 g sucrose, 44 nM benzylaminopurine, and 200 µL Silwet L-77 (OSI Specialties) at pH 5.7. Bolting Arabidopsis plants (T$_0$ generation) that were 5 to 10 cm tall were inverted into the bacterial suspension and exposed to a vacuum (>500 mm of Hg) for three to five min. Infiltrated plants were returned to standard growth conditions for seed production. Transformed seedlings (T$_1$) were identified by selection on MS medium containing 50 mg L$^{-1}$ kanamycin and 200 mg L$^{-1}$ TIMENTIN (SmithKline Beecham) and were transferred to soil.

Transformation of tobacco was accomplished using the leaf disk method of Horsch et al. (*Science* 227, 1229, (1985)).

Nitrobenzene oxidation

For the determination of lignin monomer composition, stem tissue was ground to a powder in liquid nitrogen and extracted with 20 mL of 0.1 M sodium phosphate buffer, pH 7.2 at 37° C. for 30 min followed by three extractions with 80% ethanol at 80° C. The tissue was then extracted once with acetone and completely dried. Tissue was saponified by treatment with 1.0 M NaOH at 37° C. for 24 hours, washed three times with water, once with 80% ethanol, once with acetone, and dried. Nitrobenzene oxidation of stem tissue samples was performed with a protocol modified from Iiyama et al. (*J. Sci. Food Agric.* 51, 481–491. (1990)). Samples of lignocellulosic material (5 mg each) were mixed with 500 µL of 2 M NaOH and 25 µL of nitrobenzene. This mixture was incubated in a sealed glass tube at 160° C. for 3 h. The reaction products were cooled to room temperature and 5 µL of a 20 mg mL$^{-1}$ solution of 3-ethoxy-4-hydroxybenzaldehyde in pyridine was added as an internal standard before the mixture was extracted twice with 1 mL of dichloromethane. The aqueous phase was acidified with HCl (pH 2) and extracted twice with 900 µL of ether. The combined ether phases were dried with anhydrous sodium sulfate and the ether was evaporated in a stream of nitrogen. The dried residue was resuspended in 50 µL of pyridine, 10 µL of BSA (N,O-bis-(trimethylsilyl)-trifluoracetamide) was added and 1 µL aliquots of the silylated products were analyzed using a Hewlet-Packard 5890 Series II gas chromatograph equipped with Supelco SPB I column (30 m×0.75 mm). Lignin monomer composition was calculated from the integrated areas of the peaks representing the trimethylsilylated derivatives of vanillin, syringaldehyde, vanillic acid and syringic acid. Total nitrobenzene oxidation-susceptible guaiacyl units (vanillin and vanillic acid) and syringyl units (syringaldehyde and syringic acid) were calculated following correction for recovery efficiencies of each of the products during the extraction procedure relative to the internal standard.

EXAMPLE 1

IDENTIFICATION OF THE T-DNA TAGGED ALLELE OF FAH1

A putatively T-DNA tagged fah1 mutant was identified in a collection of T-DNA tagged lines (Feldmann et al., *Mol. Gen. Genet.* 208, 1, (1987)) (Dr. Tim Caspar, Dupont, Wilmington, Del.) by screening adult plants under long wave UV light. A red fluorescent line (line 3590) was selected, and its progeny were assayed for sinapoylmalate content by TLC. The analyses indicated that line 3590 did not accumulate sinapoylmalate. Reciprocal crosses of line 3590 to a fah1–2 homozygote, followed by analysis of the F1 generation for sinapoylmalate content demonstrated that line 3590 was a new allele of fah1, and it was designated fah1–9.

Preliminary experiments indicated co-segregation of the kanamycin-resistant phenotype of the T-DNA tagged mutant with the fah1 phenotype. Selfed seed from 7 kanamycin-resistant [fah1–9× FAH1] F1 plants segregated 1:3 for kanamycin resistance (kan$^{sensitive}$ kan$^{resistant}$) and 3:1 for sinapoylmalate deficiency (FAH1:fah1). From these lines, fah1 plants gave rise to only kan$^{resistant}$, fah1 progeny. To determine the genetic distance between the T-DNA insertion and the FAH1 locus, multiple test crosses were performed between a [fah1–9×FAH1] F1 and a fah1–2 homozygote. The distance between the FAH1 locus and the T-DNA insertion was evaluated by determining the frequency at which FAH1/kan$^{sensitive}$ progeny were recovered in the test cross F1. In the absence of crossover events, all kanamycin-resistant F1 progeny would be unable to accumulate sinapoylmalate, and would thus fluoresce red under UV light. In 682 kan$^{resistant}$ F1 progeny examined, no sinapoyl-malate proficient plants were identified, indicating a very tight linkage between the T-DNA insertion site and the FAH1 locus.

EXAMPLE 2

PLASMID RESCUE AND cDNA CLONING OF THE fah1 GENE

Plasmid rescue was conducted using EcoRI-digested DNA prepared from homozygous fah1–9 plants (Behringer et al., (1992), supra). Five µg of EcoRI-digested genomic DNA was incubated with 125 U T4 DNA ligase overnight at 14° C. in a final volume of 1 mL. The ligation mixture was concentrated approximately four fold by two extractions with equal volumes of 2-butanol, and was then ethanol precipitated and electroporated into competent DH5-α cells as described (Newman et al., (1994), supra).

DNA from rescued plasmids was double digested with EcoRI and SalI. Plasmids generated from internal T-DNA sequences were identified by the presence of triplet bands at 3.8, 2.4 and 1.2 kb and were discarded. One plasmid (pCC1) giving rise to the expected 3.8 kb band plus a novel 5.6 kb band was identified as putative external right border plasmid. Using a SacII/EcoRI fragment of pCC1 that appeared to represent Arabidopsis DNA, putative cDNA (pCC30) clones for F5H were identified. The putative F5H clone carried a 1.9 kb SalI-NotI insert, the sequence of which was determined. BLASTX analysis (Altschul et al., *J Mol. Biol.* 215, 403, (1990)) indicated that this cDNA encodes a cytochrome P450-dependent monooxygenase, consistent with earlier reports that (i) the fah1 mutant is defective in F5H (Chapple et al., supra) and (ii) F5H is a cytochrome P450-dependent monooxygenase (Grand, supra).

Southern and Northern Blot analysis

To determine whether the putative F5H cDNA actually represented the gene that was disrupted in the T-DNA tagged line Southern and northern analysis was used to characterize the available fah1 mutants using the putative F5H cDNA.

Figure 6:
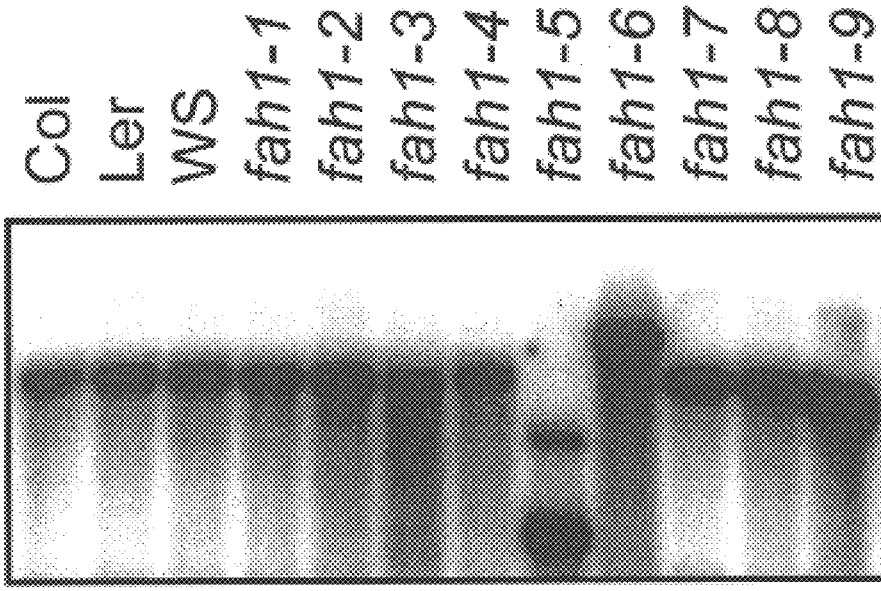
FIG. 6 illustrates a Southern blot analysis comparing hybridization of the F5H cDNA to EcoRI digested genomic DNA isolated from wild type Arabidopsis thaliana and a number of fah1 mutants.

FIG. 6 shows a Southern blot comparing hybridization of the F5H cDNA to EcoRI-digested genomic DNA isolated from wild type (ecotypes Columbia (Col), Landsberg erecta (LER), and Wassilewskija (WS)) and the nine fah1 alleles including the T-DNA tagged fah1–9 allele. WS is the ecotype from which the T-DNA tagged line was generated.

These data indicated the presence of a restriction fragment length polymorphism between the tagged line and the wild type. These data also indicates a restriction fragment length polymorphism in the fah1–8 allele which was generated with fast neutrons, a technique reported to cause deletion mutations.

As shown in FIG. 6 the genomic DNA of the fah1–8 and fah1–9 (the T-DNA tagged line) alleles is disrupted in the region corresponding to the putative F5H cDNA. These data also indicate that F5H is encoded by a single gene in Arabidopsis as expected considering that the mutation in the fah1 mutant segregates as a single Mendelian gene. These data provide the first indication that the putative F5H cDNA corresponds to the gene that is disrupted in the fah1 mutants.

Figure 7:
FIG. 7 is a Northern blot analysis comparing hybridization of the F5H cDNA to RNA isolated from wild type Arabidopsis thaliana and a number of fah1 mutants.

Plant material homozygous for nine independently-derived fah1 alleles was surveyed for the abundance of transcript corresponding to the putative F5H cDNA using Northern blot analysis. The data is shown in FIG. 7.

As can be seen from the data, the putative F5H mRNA was represented at similar levels in leaf tissue of Columbia, Landsberg erecta and Wassilewskija ecotypes, and in the EMS-induced fah1—1, fah1–4, and fah1–5, as well as the fast neutron-induced fah1–7. Transcript abundance was substantially reduced in leaves from plants homozygous for the fah1–2, fah1–3 and fah1–6, all of which were EMS-induced, the fast neutron-induced mutant fah1–8 and in the tagged line fah1–9. The mRNA in fah1–8 mutant also appears to be truncated. These data provided strong evidence that the cDNA clone that had been identified is encoded by the FAH1 locus.

EXAMPLE 3

DEMONSTRATION OF THE IDENTITY OF THE F5H cDNA BY TRANSFORMATION OF fah1 MUTANT PLANTS WITH WILDTYPE F5H AND RESTORATION OF SINAPOYLMALATE ACCUMULATION In order to demonstrate the identity of the F5H gene at the functional level, the transformation-competent pBIC20 cosmid library (Meyer et al., supra) was screened for corresponding genomic clones using the full length F5H cDNA as a probe. A clone (pBIC20-F5H) carrying a genomic insert of 17 kb that contains 2.2 kb of sequence upstream of the putative F5H start codon and 12.5 kb of sequence downstream of the stop codon of the F5H gene (FIG. 2) was transformed into the fah1–2 mutant by vacuum infiltration. Thirty independent infiltration experiments were performed, and 167 kanamycin-resistant seedlings, representing at least 3 transformants from each infiltration, were transferred to soil and were analyzed with respect to sinapic acid-derived secondary metabolites. Of these plants, 164 accumulated sinapoylmalate in their leaf tissue as determined by TLC (FIG. 3). These complementation data indicate that the gene defective in the fall mutant is present on the binary cosmid pBIC20-FSH.

To delimit the region of DNA on the pBIC20-FSH cosmid responsible for complementation of the mutant phenotype, a 2.7 kB fragment of the F5H genomic sequence was fused downstream of the cauliflower mosaic virus 35S promoter in the binary plasmid pGA482 and this construct (pGA482-35S-F5H) (FIG. 2) was transformed into the fah1–2 mutant. The presence of sinapoylmalate in 109 out of 110 transgenic lines analyzed by TLC or by in vivo fluorescence under UV light indicated that the fah1 mutant phenotype had been complemented (FIG. 3). These data provide conclusive evidence that the F5H cDNA has been identified.

EXAMPLE 4

DNA SEQUENCING OF THE F5H cDNA AND GENOMIC CLONES

The F5H cDNA and a 5156 bp HindIII-XhoI fragment of the pBIC20-F5H genomic clone were both fully sequenced on both strands and the sequence of the F5H protein (SEQ ID NO.: 2) was inferred from the cDNA sequence (FIG. 8). The sequence of the Arabidopsis thaliana F5H cDNA is given in SEQ ID NO.: 1. The sequence of the Arabidopsis thaliana F5H genomic clone is given in SEQ ID NO.: 3.

EXAMPLE 5

MODIFICATION OF LIGNIN MONOMER COMPOSITION IN TRANSGENIC PLANTS OVEREXPRESSING F5H

Generation of Transgenic Plants Ectopically Expressing the F5H Gene

Using an adaptor-based cloning strategy, regulatory sequences 5' of the translation initiation site of the F5H gene were replaced with the strong constitutive cauliflower mosaic virus 35S promoter (Odell et al., Nature 313, 810–812. (1985)), as shown in FIG. 2. The resulting construct carries 2719 bp of the F5H genomic sequence driven by the cauliflower mosaic virus 35S promoter fused 50 bp upstream of the inferred ATG start codon. As a result, the cauliflower mosaic virus 35S promoter drives the expression of the F5H gene by using the transcription start site of the viral promoter and the termination signal present on the F5H genomic sequence. This expression cassette for ectopic expression of F5H was inserted into the T-DNA of the binary vector pGA482 (An, G. (1987), *Binary Ti vectors for plant transformation and promoter analysis* in: *Methods in enzymology*. Wu, R. ed. Academic Press, N.Y. 153: 292–305) and introduced into *Agrobacterium tumefaciens* by electroporation.

Transgenic Arabidopsis plants of the ecotype Columbia that were homozygous for the fah1–2 (Chapple et al., supra) allele were transformed with Agrobacterium cultures harboring the pGA482-35S-F5H construct according to the method of Bent et al. (supra). Transgenic plants of the T2 and T3 generation were identified by selection on media containing kanamycin and subsequently transferred to soil.

Determination of lignin monomer composition of Arabidopsis stem tissue

Total stem tissue was harvested from 4 week old plants that had been grown in soil at 22° C. under a 16 h/8 h light/dark photoperiod. Nitrobenzene oxidation analysis generated mol % syringyl values for 9 different transformant lines (Table 1) ranging from 5.06±0.17 mol % to 28.8±0.92 mol % as opposed to the wildtype control which demonstrated a value of 18.4±0.91 mol %. The fah1–2 mutant background in which the transgenic lines were generated completely lacks syringyl lignin (Table 1). The low expression of the F5H transgene in a genetic background that lacks endogenous F5H message explains how line 88 can have syringyl lignin levels that are lower than wild type.

In addition to Arabidopsis, tobacco plants were transformed in a similar fashion with the F5H gene under control of the cauliflower mosaic virus 35S promoter. T2 and T3 positive transformants were screened and analyzed for lignin modification and the data is given in Table 2. Nitrobenzene oxidation analysis of tobacco leaf midribs generated mol % syringyl values for 4 different transformant lines (Table 2) ranging from 22.4±1.53 mol % to 40.0±1.86 mol % as opposed to the wildtype control which demonstrated a value of 14.3±1.09 mol %.

The data in Tables 1 and 2 clearly demonstrate that over-expression of the F5H gene in transgenic plants results in the modification of lignin monomer composition. The transformed plant is reasonably expected to have syringyl lignin monomer content that is from about 0 mol % to about 95 mol % as measured in whole plant tissue.

What is claimed is:

1. An isolated nucleic-acid fragment encoding an active plant F5H enzyme having an amino acid sequence selected from the group consisting of (1) the amino acid sequence of SEQ ID NO: 2, and (2) an amino acid sequence of SEQ ID NO: 2 encompassing amino acid substitutions, additions and deletions that do not alter the function of the active plant F5H enzyme.

2. A chimeric gene causing altered guaiacyl:syringyl lignin monomer ratios in a plant cell transformed with the chimeric gene, the chimeric gene comprising:
   a regulatory sequence; and
   a nucleic-acid fragment encoding an active plant F5H enzyme having an amino acid sequence selected from the group consisting of (1) the amino acid sequence of SEQ ID NO: 2, and (2) an amino acid sequence of SEQ ID NO: 2 encompassing amino acid substitutions, additions and deletions that do not alter the function of the active plant F5H enzyme; and
   wherein the nucleic-acid fragment is operably linked in either sense or antisense orientation to the regulatory sequence.

3. The chimeric gene of claim 2 wherein the nucleic acid fragment is operably linked in the sense orientation to at least one regulatory sequence.

4. The chimeric gene of claim 2 wherein the regulatory sequence comprises a promoter selected from the group consisting of cauliflower mosaic virus 35S promoter, the promoter for the phenylalanine ammonia lyase gene and the promoter for the p-coumaroyl CoA ligase gene.

5. The chimeric gene of claim 2, wherein the regulatory sequence comprises an endogenous plant promoter effective for controlling expression of a plant F5H gene.

6. An isolated nucleic-acid fragment selected from the group consisting of the nucleic acid fragment of SEQ ID NO: 1, the nucleic acid fragment of SEQ ID NO: 3 and a nucleic acid fragment of SEQ ID NO: 1 or SEQ ID NO: 3 encompassing base changes that do not alter the function of the encoded plant F5H enzyme.

7. A chimeric gene causing altered guaiacyl:syringyl lignin monomer ratios in a plant cell transformed with the chimeric gene, the chimeric gene comprising an isolated nucleic-acid fragment selected from the group consisting of the nucleic acid fragment of SEQ ID NO: 1, the nucleic acid fragment of SEQ ID NO: 3 and a nucleic acid fragment of SEQ ID NO: 1 or SEQ ID NO: 3 encompassing base changes that do not alter the function of the encoded plant F5H enzyme, operably linked in either sense or antisense orientation to at least one regulatory sequence.

8. The chimeric gene of claim 7 wherein the nucleic acid fragment is operably linked in the sense orientation to at least one regulatory sequence.

9. The chimeric gene of claim 7, wherein the at least one regulatory sequence comprises a promoter selected from the group consisting of cauliflower mosaic virus 35S promoter, the promoter for the phenylalanine ammonia lyase gene and the promoter for the p-coumaroyl CoA ligase gene.

10. The chimeric gene of claim 7 wherein the at least one regulatory sequence comprises an endogenous plant promoter effective for controlling expression of a plant F5H gene.

11. A transformed plant having altered guaiacyl:syringyl lignin monomer ratios relative to the ratios of an untransformed plant, comprising a host plant having incorporated therein an expressible chimeric gene causing altered guaiacyl:syringyl lignin monomer ratios in a plant cell transformed with the chimeric gene, the chimeric gene comprising an isolated nucleic-acid fragment selected from the group consisting of the nucleic acid fragment of SEQ ID NO: 1, the nucleic acid fragment of SEQ ID NO: 3 and a nucleic acid fragment of SEQ ID NO: 1 or SEQ ID NO: 3 encompassing base changes that do not alter the function of the encoded plant F5H enzyme, operably linked in either sense or antisense orientation to at least one regulatory sequence.

12. The transformed plant of claim 11 wherein the syringyl lignin monomer content is from about 0 mol % to about 95 mol % as measured in whole plant tissue.

13. The transformed plant of claim 12 wherein the host plant is selected from the group consisting of alfalfa (Medicago sp.), rice (Oryza sp.), maize (Zea mays), oil seed rape (Brassica sp.), forage grasses, (Arabidopsis sp.), tobacco (Nicotiana sp.), eucalyptus (Eucalyptus sp.), pine (Pinus sp.), spruce (Picea sp.) and poplar (Populus sp.).

14. The transformed plant of claim 12, wherein the host plant is a tree crop.

15. A method of altering the activity of F5H enzyme in a plant, comprising:
(i) transforming a cell, tissue or organ from a host plant with a chimeric gene causing altered guaiacyl:syringyl lignin monomer ratios in a plant cell transformed with the chimeric gene, the chimeric gene comprising an isolated nucleic-acid fragment selected from the group consisting of the nucleic acid fragment of SEQ ID NO: 1, the nucleic acid fragment of SEQ ID NO: 3 and a nucleic acid fragment of SEQ ID NO: 1 or SEQ ID NO: 3 encompassing base changes that do not alter the function of the encoded plant F5H enzyme, operably linked in either sense or antisense orientation to at least one regulatory sequence wherein the chimeric gene is expressed;
(ii) selecting a transformed cell, cell callus, somatic embryo, or seed which contains the chimeric gene;
(iii) regenerating a whole plant from the selected transformed cell, cell callus, somatic embryo, or seed; and
(iv) selecting a regenerated whole plant which has a phenotype selected from the group consisting of (1) accumulation of compounds derived from sinapic acid and (2) an altered syringyl lignin monomer content relative to an untransformed host plant;
wherein F5H enzyme activity is altered in the plant.

16. A method of altering the content or composition of lignin in a plant, comprising stably incorporating into the genome of the plant a chimeric gene causing altered guaiacyl:syringyl lignin monomer ratios in a plant cell transformed with the chimeric gene, the chimeric gene comprising an isolated nucleic-acid fragment selected from the group consisting of the nucleic acid fragment of SEQ ID NO: 1, the nucleic acid fragment of SEQ ID NO: 3 and a nucleic acid fragment of SEQ ID NO: 1 or SEQ ID NO: 3 encompassing base changes that do not alter the function of the encoded plant F5H enzyme, operably linked in either sense or antisense orientation to at least one regulatory sequence;
wherein said incorporating is achieved by transformation means whereby the incorporated chimeric gene expresses F5H enzyme and whereby guaiacyl:syringyl lignin monomer content or composition is altered from that of the untransformed host plant.

17. A transformed plant having altered guaiacyl:syringyl lignin monomer ratios relative to the ratios of an untransformed plant, comprising a host plant having incorporated therein an expressible chimeric gene causing altered guaiacyl:syringyl lignin monomer ratios in a plant cell transformed with the chimeric gene;
wherein the chimeric gene comprises:
a regulatory sequence; and
a nucleic-acid fragment encoding an active plant F5H enzyme having an amino acid sequence selected from the group consisting of (1) the amino acid sequence of SEQ ID NO: 2, and (2) an amino acid sequence of SEQ ID NO: 2 encompassing amino acid substitutions, additions and deletions that do not alter the function of the active plant F5H enzyme; and
wherein the nucleic-acid fragment is operably linked in either sense or antisense orientation to the regulatory sequence.

18. The transformed plant of claim 17 wherein the syringyl lignin monomer content is from about 0 mol % to about 95 mol % as measured in whole plant tissue.

19. The transformed plant of claim 17 wherein the host plant is selected from the group consisting of alfalfa (Medicago sp.), rice (Oryza sp.), maize (Zea mays), oil seed rape (Brassica sp.), forage grasses, (Arabidopsis sp.), tobacco (Nicotiana sp.), eucalyptus (Eucalyptus sp.), pine (Pinus sp.), spruce (Picea sp.) and poplar (Populus sp.).

20. The transformed plant of claim 17 wherein the host plant is a tree crop.

21. A method of altering the activity of F5H enzyme in a plant, comprising:
(i) transforming a cell, tissue or organ from a host plant with a chimeric gene causing altered guaiacyl:syringyl lignin monomer ratios in a plant cell transformed with the chimeric gene,
(ii) selecting a transformed cell, cell callus, somatic embryo, or seed which contains the chimeric gene;
(iii) regenerating a whole plant from the selected transformed cell, cell callus, somatic embryo, or seed; and
(iv) selecting a regenerated whole plant which has a phenotype selected from the group consisting of (1) accumulation of compounds derived from sinapic acid or (2) an altered syringyl lignin monomer content relative to an untransformed host plant;
wherein the chimeric gene comprises a regulatory sequence and a nucleic-acid fragment encoding an active plant F5H enzyme having an amino acid sequence selected from the group consisting of (1) the amino acid sequence of SEQ ID NO: 2, and (2) an amino acid sequence of SEQ ID NO: 2 encompassing amino acid substitutions, additions and deletions that do not alter the function of the active plant F5H enzyme;
wherein the nucleic-acid fragment is operably linked in either sense or antisense orientation to the regulatory sequence; and
wherein F5H enzyme activity is altered in the plant.

22. A method of altering the content or composition of lignin in a plant, comprising stably incorporating into the genome of the plant a chimeric gene causing altered guaiacyl:syringyl lignin monomer ratios in a plant cell transformed with the chimeric gene;
  wherein the chimeric gene comprises a regulatory sequence and a nucleic-acid fragment encoding an active plant F5H enzyme having an amino acid sequence selected from the group consisting of (1) the amino acid sequence of SEQ ID NO: 2, and (2) an amino acid sequence of SEQ ID NO: 2 encompassing amino acid substitutions, additions and deletions that do not alter the function of the active plant F5H enzyme;
  wherein the nucleic-acid fragment is operably linked in either sense or antisense orientation to the regulatory sequence; and
  wherein said incorporating is achieved by transformation means whereby the incorporated chimeric gene expresses F5H enzyme and whereby guaiacyl:syringyl lignin monomer content or composition is altered from that of the untransformed host plant.

23. A method for altering the activity of F5H enzyme in a plant, comprising:
  providing an expressable chimeric gene comprising a nucleotide sequence encoding an active plant F5H enzyme having an amino acid sequence selected from the group consisting of (1) the amino acid sequence of SEQ ID NO: 2, and (2) an amino acid sequence of SEQ ID NO: 2 encompassing amino acid substitutions, additions and deletions that do not alter the function of the enzyme; and
  transforming a plant with the chimeric gene to provide a transformed plant, wherein the transformed plant expresses the chimeric gene, and wherein F5H enzyme activity is altered in the plant.

24. The method according to claim 23, wherein the nucleotide sequence is selected from the group consisting of the sequence set forth in SEQ ID NO: 1 and the sequence set forth in SEQ ID NO: 3.

* * * * *

SEQUENCE LISTING

<160> NUMBER OF SEQ ID NOS: 3

<210> SEQ ID NO 1
<211> LENGTH: 1838
<212> TYPE: DNA
<213> ORGANISM: Arabidopsis thaliana

<400> SEQUENCE: SEQ ID NO: 1

| | | | | | |
|---|---|---|---|---|---|
| aaaaaaaaca | ctcaatatgg | agtcttctat | atcacaaaca | ctaagcaaac | tatcagatcc | 60 |
| cacgacgtct | cttgtcatcg | ttgtctctct | tttcatcttc | atcagcttca | tcacacggcg | 120 |
| gcgaaggcct | ccatatcctc | ccggtccacg | aggttggccc | atcataggca | acatgttaat | 180 |
| gatggaccaa | ctcacccacc | gtggtttagc | caatttagct | aaaaagtatg | gcggattgtg | 240 |
| ccatctccgc | atgggattcc | tccatatgta | cgctgtctca | tcacccgagg | tggctcgaca | 300 |
| agtccttcaa | gtccaagaca | gcgtcttctc | gaaccggcct | gcaactatag | ctataagcta | 360 |
| tctgacttac | gaccgagcgg | acatggcttt | cgctcactac | ggaccgtttt | ggagacagat | 420 |
| gagaaaagtg | tgtgtcatga | aggtgtttag | ccgtaaaaga | gctgagtcat | gggcttcagt | 480 |
| tcgtgatgaa | gtggacaaaa | tggtccggtc | ggtctcttgt | aacgttggta | agcctataaa | 540 |
| cgtcggggag | caaattttg | cactgacccg | caacataact | taccgggcag | cgtttgggtc | 600 |
| agcctgcgag | aagggacaag | acgagttcat | aagaatctta | caagagttct | ctaagctttt | 660 |
| tggagccttc | aacgtagcgg | atttcatacc | atatttcggg | tggatcgatc | cgcaagggat | 720 |
| aaacaagcgg | ctcgtgaagg | cccgtaatga | tctagacgga | tttattgacg | atattatcga | 780 |
| tgaacatatg | aagaagaagg | agaatcaaaa | cgctgtggat | gatggggatg | ttgtcgatac | 840 |
| cgatatggtt | gatgatcttc | ttgcttttta | cagtgaagag | gccaaattag | tcagtgagac | 900 |
| agcggatctt | caaaattcca | tcaaacttac | ccgtgacaat | atcaaagcaa | tcatcatgga | 960 |
| cgttatgttt | ggaggaacgg | aaacggtagc | gtcggcgata | gagtgggcct | taacggagtt | 1020 |
| attacggagc | cccgaggatc | taaaacgggt | ccaacaagaa | ctcgccgaag | tcgttggact | 1080 |
| tgacagacga | gttgaagaat | ccgacatcga | gaagttgact | tatctcaaat | gcacactcaa | 1140 |
| agaaacccta | aggatgcacc | caccgatccc | tctcctcctc | cacgaaaccg | cggaggacac | 1200 |
| tagtatcgac | ggtttcttca | ttcccaagaa | atctcgtgtg | atgatcaacg | cgtttgccat | 1260 |
| aggacgcgac | ccaacctctt | ggactgaccc | ggacacgttt | agaccatcga | ggttttttgga | 1320 |
| accgggcgta | ccggatttca | aagggagcaa | tttcgagttt | ataccgttcg | ggtcgggtcg | 1380 |
| tagatcgtgc | ccgggtatgc | aactagggtt | atacgcgctt | gacttagccg | tggctcatat | 1440 |
| attacattgc | ttcacgtgga | aattacctga | tgggatgaaa | ccaagtgagc | tcgacatgaa | 1500 |
| tgatgtgttt | ggtctcacgg | ctcctaaagc | cacgcggctt | ttcgccgtgc | caaccacgcg | 1560 |
| cctcatctgt | gctctttaag | tttatggttc | gagtcacgtg | gcaggggtt | tggtatggtg | 1620 |
| aaaactgaaa | agtttgaagt | tgccctcatc | gaggatttgt | ggatgtcata | tgtatgtatg | 1680 |
| tgtatacacg | tgtgttctga | tgaaaacaga | tttggctctt | tgtttgccct | ttttttttt | 1740 |
| ttctttaatg | gggatttttcc | ttgaatgaaa | tgtaacagta | aaaataagat | ttttttcaat | 1800 |
| aagtaattta | gcatgttgca | aaaaaaaaaa | aaaaaaa | | | 1838 |

<210> SEQ ID NO 2
<211> LENGTH: 520
<212> TYPE: PRT
<213> ORGANISM: Artificial
<220> FEATURE:

<223> OTHER INFORMATION: Sequence is deduced from DNA sequence of SEQ ID NO:1

<400> SEQUENCE: SEQ ID NO: 2

```
Met Glu Ser Ser Ile Ser Gln Thr Leu Ser Lys Leu Ser Asp Pro Thr
 1               5                  10                  15

Thr Ser Leu Val Ile Val Val Ser Leu Phe Ile Phe Ile Ser Phe Ile
                20                  25                  30

Thr Arg Arg Arg Arg Pro Pro Tyr Pro Pro Gly Pro Arg Gly Trp Pro
                35                  40                  45

Ile Ile Gly Asn Met Leu Met Met Asp Gln Leu Thr His Arg Gly Leu
 50                  55                  60

Ala Asn Leu Ala Lys Lys Tyr Gly Gly Leu Cys His Leu Arg Met Gly
 65                  70                  75                  80

Phe Leu His Met Tyr Ala Val Ser Ser Pro Glu Val Ala Arg Gln Val
                85                  90                  95

Leu Gln Val Gln Asp Ser Val Phe Ser Asn Arg Pro Ala Thr Ile Ala
                100                 105                 110

Ile Ser Tyr Leu Thr Tyr Asp Arg Ala Asp Met Ala Phe Ala His Tyr
                115                 120                 125

Gly Pro Phe Trp Arg Gln Met Arg Lys Val Cys Val Met Lys Val Phe
 130                 135                 140

Ser Arg Lys Arg Ala Glu Ser Trp Ala Ser Val Arg Asp Glu Val Asp
 145                 150                 155                 160

Lys Met Val Arg Ser Val Ser Cys Asn Val Gly Lys Pro Ile Asn Val
                165                 170                 175

Gly Glu Gln Ile Phe Ala Leu Thr Arg Asn Ile Thr Tyr Arg Ala Ala
                180                 185                 190

Phe Gly Ser Ala Cys Glu Lys Gly Gln Asp Glu Phe Ile Arg Ile Leu
                195                 200                 205

Gln Glu Phe Ser Lys Leu Phe Gly Ala Phe Asn Val Ala Asp Phe Ile
 210                 215                 220

Pro Tyr Phe Gly Trp Ile Asp Pro Gln Gly Ile Asn Lys Arg Leu Val
 225                 230                 235                 240

Lys Ala Arg Asn Asp Leu Asp Gly Phe Ile Asp Asp Ile Ile Asp Glu
                245                 250                 255

His Met Lys Lys Lys Glu Asn Gln Asn Ala Val Asp Asp Gly Asp Val
                260                 265                 270

Val Asp Thr Asp Met Val Asp Leu Leu Ala Phe Tyr Ser Glu Glu
                275                 280                 285

Ala Lys Leu Val Ser Glu Thr Ala Asp Leu Gln Asn Ser Ile Lys Leu
 290                 295                 300

Thr Arg Asp Asn Ile Lys Ala Ile Ile Met Asp Val Met Phe Gly Gly
 305                 310                 315                 320

Thr Glu Thr Val Ala Ser Ala Ile Glu Trp Ala Leu Thr Glu Leu Leu
                325                 330                 335

Arg Ser Pro Glu Asp Leu Lys Arg Val Gln Gln Glu Leu Ala Glu Val
                340                 345                 350

Val Gly Leu Asp Arg Arg Val Glu Glu Ser Asp Ile Glu Lys Leu Thr
                355                 360                 365

Tyr Leu Lys Cys Thr Leu Lys Glu Thr Leu Arg Met His Pro Pro Ile
 370                 375                 380

Pro Leu Leu Leu His Glu Thr Ala Glu Asp Thr Ser Ile Asp Gly Phe
 385                 390                 395                 400
```

```
Phe Ile Pro Lys Lys Ser Arg Val Met Ile Asn Ala Phe Ala Ile Gly
                405                 410                 415

Arg Asp Pro Thr Ser Trp Thr Asp Pro Asp Thr Phe Arg Pro Ser Arg
            420                 425                 430

Phe Leu Glu Pro Gly Val Pro Asp Phe Lys Gly Ser Asn Phe Glu Phe
        435                 440                 445

Ile Pro Phe Gly Ser Gly Arg Arg Ser Cys Pro Gly Met Gln Leu Gly
    450                 455                 460

Leu Tyr Ala Leu Asp Leu Ala Val Ala His Ile Leu His Cys Phe Thr
465                 470                 475                 480

Trp Lys Leu Pro Asp Gly Met Lys Pro Ser Glu Leu Asp Met Asn Asp
            485                 490                 495

Val Phe Gly Leu Thr Ala Pro Lys Ala Thr Arg Leu Phe Ala Val Pro
        500                 505                 510

Thr Thr Arg Leu Ile Cys Ala Leu
            515                 520

<210> SEQ ID NO 3
<211> LENGTH: 5156
<212> TYPE: DNA
<213> ORGANISM: Arabidopsis thaliana

<400> SEQUENCE: SEQ ID NO: 3 aagcttatgt atttccttat aaccatttta ttctgtatat aggggacag aaacataata      60
agtaacaaat agtggtttta ttttttttaaa tatacaaaaa ctgtttaacc attttatttc   120
ttggttagca aaattttgat atattcttaa gaaactaata ttttaggttg atatattgca   180
gtcactaaat agttttaaaa gacacgaagt tggtaagaac aggcatatat tattcgattt   240
aattaggaat gcttatgtta atctgattcg actaattaga aacgacgata ctatgagctc   300
atagatggtc ccacgaccca ctctcccatt tgatcaatat tcaactgagc aatgaaacta   360
attaaaaacg tggttagatt aaaaaaataa attgtgcagg tagcggatat ataatactag   420
tagggggttaa aaataaaata aaacaccaca gtattaaatt tttgtttcaa agtattatc   480
aatagttttt ttgcttcaaa aatatcacaa attttgtat gaaatatttc tttaacgaaa   540
ataaattaaa taaaatttaa aatttatatt tggagttcta ttttttaattt agagttttta   600
ttgttaccac atttttgaa ttattctaat attaatttgt gatattatta caaaaagtaa   660
aaatatgata ttttagaata ctattatcga tatttgatat tattgacctt agctttgttt   720
gggtggagac atgtgattat cttattacct ttttattcca tgaaactaca gagttcgcca   780
ggtaccatac atgcacacac cctcgtgaag ccgtgactta atatgatcta gaacttaaat   840
agtactacta attgtgtcat ttgaactttc tcctatgtcg gtttcacttc atgtatcgca   900
gaacaggtgg aatacagtgt ccttgagttt cacccaaatc ggtccaattt tgtgatatat   960
attgcgatac agacatacag cctacagagt tttgtcttag cccactggtt ggcaaacgaa  1020
attgtctttta ttttttatg ttttgttgtc aatgtgtctt tgttttttaac tagattgagg  1080
tttaattta atacatttgt tagtttacag attatgcagt gtaatctgat aatgtaagtt   1140
gaactgcgtt ggtcaaagtc ttgtgtaacg cactgtatct aaattgtgag taacgacaaa  1200
ataattaaaa ttaaaggacc ttcaagtatt attagtatct ctgtctaaga tgcacaggta  1260
ttcagtaata gtaataaata attacttgta taattaatat ctaattagta aaccttgtgt  1320
ctaaacctaa atgagcataa atccaaaagc aaaaatctaa acctaactga aaagtcatt   1380
acgaaaaaaa gaaaaaaaaa agagaaaaaa ctacctgaaa agtcatgcac aacgttcatc  1440
```

```
ttggctaaat ttatttagtt tattaaatac aaaaatggcg agtttctgga gtttgttgaa    1500
aatatatttg tttagccact ttagaatttc ttgttttaat ttgttattaa gatatatcga    1560
gataatgcgt ttatatcacc aatattttg ccaaactagt cctatacagt cattttcaa     1620 cagctatgtt cactaatttta aaacccactg aaagtcaatc atgattcgtc atatttatat   1680
gctcgaattc agtaaaatcc gtttggtata ctatttattt cgtataagta tgtaattcca   1740
ctagatttcc ttaaactaaa ttatatattt acataattgt tttctttaaa agtctacaac   1800
agttattaag ttataggaaa ttattctttt tattttttt ttttttttagg aaattatttc    1860 ttttgcaaca catttgtcgt ttgcaaactt ttaaaagaaa ataaatgatt gttataattg    1920
attacatttc agtttatgac agatttttt tatctaacct ttaatgtttg tttccctgtt     1980
tttaggaaaa tcataccaaa atatatttgt gatcacagta aatcacgaaa tagttatgac   2040
caagattttc aaagtaatac ttagaatcct attaaataaa cgaaatttta ggaagaaata   2100
atcaagattt taggaaacga tttgagcaag gatttagaag atttgaatct ttaattaaat   2160
attttcattc ctaaataatt aatgctagtg gcataatatt gtaaataagt tcaagtacat   2220
gattaatttg ttaaaatggt tgaaaaatat atatatgtag atttttttcaa aagtatact   2280 aattatttc atattttcaa gaaaatataa gaaatggtgt gtacatatat ggatgaagaa    2340
atttaagtag ataatacaaa aatgtcaaaa aaagggacca cacaatttga ttataaaacc   2400
tacctctcta atcacatccc aaaatggaga actttgcctc ctgacaacat ttcagaaaat   2460
aatcgaatcc aaaaaaaaca ctcaatatgg agtcttctat atcacaaaca ctaagcaaac   2520
tatcagatcc cacgacgtct cttgtcatcg ttgtctctct tttcatcttc atcagcttca   2580
tcacacggcg gcgaaggcct ccatatcctc ccggtccacg aggttggccc atcataggca   2640
acatgttaat gatggaccaa ctcacccacc gtggtttagc caatttagct aaaaagtatg   2700
gcggattgtg ccatctccgc atgggattcc tccatatgta cgctgtctca tcacccgagg   2760
tggctcgaca agtccttcaa gtccaagaca gcgtcttctc gaaccggcct gcaactatag   2820
ctataagcta tctgacttac gaccgagcgg acatggcttt cgctcactac ggaccgtttt   2880
ggagacagat gagaaaagtg tgtgtcatga aggtgtttag ccgtaaaaga gctgagtcat   2940
gggcttcagt tcgtgatgaa gtggacaaaa tggtccggtc ggtctcttgt aacgttggta   3000
agctacttca catattcacc actcttgcta tatatatgtg caattaaaca aatatgtaaa   3060
aagtgaaagt actcatttct tctttctta gtatgtactt taacatttaa ccaaaacaat    3120
tgtaggtaag cctataaacg tcggggagca aattttgca ctgacccgca ataaactta    3180 ccgggcagcg tttgggtcag cctgcgaaa gggacaagac gagttcataa gaatcttaca   3240
agagttctct aagcttttg gagccttcaa cgtagcggat ttcataccat atttcgggtg   3300
gatcgatccg caagggataa acaagcggct cgtgaaggcc cgtaatgatc tagacggatt   3360
tattgacgat attatcgatg aacatatgaa gaagaaggag aatcaaaacg ctgtggatga   3420 tgggatgtt gtcgataccg atatggttga tgatcttctt gcttttaca gtgaagaggc     3480 caaattagtc agtgagacag cggatcttca aaattccatc aaacttaccc gtgacaatat   3540
caaagcaatc atcatggtaa ttatatttca aaaagcacta gtcatagtca tgtttcttaa   3600
tgcgttacgt aataatactt atccattgac cagttatttt ctcctaagtt tttttgtttg   3660
aattaggaag gtaatttct attttactag agaaagcaac agattttagc atgatctttt    3720
tttaatatat atagaagcat tgaatattca gatctacaat aattatgaaa ctaatgaaga   3780
gacaaaaaat ggagagagaa aaaagaaaga gtggactagt gtggatatat ttaattctaa   3840
```

```
tttgatttta ttaggacgtt atatttaatt ctaatttgat ttttttattt gattttatta    3900
ggacgttatg tttggaggaa cggaaacggt agcgtcggcg atagagtggg ccttaacgga    3960
gttattacgg agccccgagg atctaaaacg ggtccaacaa gaactcgccg aagtcgttgg    4020
acttgacaga cgagttgaag aatccgacat cgagaagttg acttatctca aatgcacact    4080
caaagaaacc ctaaggatgc acccaccgat ccctctcctc ctccacgaaa ccgcggagga    4140
cactagtatc gacggtttct tcattcccaa gaaatctcgt gtgatgatca acgcgtttgc    4200
cataggacgc gacccaacct cttggactga cccggacacg tttagaccat cgaggttttt    4260
ggaaccgggc gtaccggatt tcaaagggag caatttcgag tttataccgt tcgggtcggg    4320
tcgtagatcg tgcccgggta tgcaactagg gttatacgcg cttgacttag ccgtggctca    4380
tatattacat tgcttcacgt ggaaattacc tgatgggatg aaaccaagtg agctcgacat    4440
gaatgatgtg tttggtctca cggctcctaa agccacgcgg cttttcgccg tgccaaccac    4500
gcgcctcatc tgtgctcttt aagtttatgg ttcgagtcac gtggcagggg gtttggtatg    4560
gtgaaaactg aaaagtttga agttgccctc atcgaggatt tgtggatgtc atatgtatgt    4620
atgtgtatac acgtgtgttc tgatgaaaac agatttggct ctttgtttgc ccttttttt    4680 tttttcttta atggggattt tccttgaatg aaatgtaaca gtaaaaataa gatttttttc    4740
aataagtaat ttagcatgtt gcaaagatcg atcttggatg agaacttcta cttaaaaaaa    4800
aaaaaaaaat ttttttttag ttatttcacc tttttctttt gttctggttg tatggttgcc    4860
attgtgtcaa ttaggggctg gaagttcgct ggttaaggct aaatcagagt taagttata    4920 attttacaag cccaacaaaa ggtcgcagat taaaaccaca tgatatttat aaaaaaaatt    4980
ctaaggtttt tattagtttt attttcagtt tactgagtac tatttacttt tttatttttt    5040
gcaaataaat gtattttatc atatttatgt tttttgttat aaactccaaa catacaggtt    5100
tcattaccta aaaaagaca gagtggtttc gttaattttg tttcattaat ctcgag        5156
```